US008703818B2

(12) United States Patent
Green

(10) Patent No.: US 8,703,818 B2
(45) Date of Patent: Apr. 22, 2014

(54) COMPOSITIONS AND METHODS COMPRISING C16:1N7-PALMITOLEATE

(75) Inventor: Jeffrey Green, University Heights, OH (US)

(73) Assignee: Tersus Pharmaceuticals, LLC, Mentor, OH (US)

( * ) Notice: Subject to any disclaimer, the term of this patent is extended or adjusted under 35 U.S.C. 154(b) by 0 days.

(21) Appl. No.: 13/411,187

(22) Filed: Mar. 2, 2012

(65) Prior Publication Data
US 2012/0225941 A1 Sep. 6, 2012

Related U.S. Application Data
(60) Provisional application No. 61/449,015, filed on Mar. 3, 2011.

(51) Int. Cl.
*A01N 37/00* (2006.01)
*A61K 47/00* (2006.01)
*A23L 1/30* (2006.01)

(52) U.S. Cl.
USPC .......................... 514/560; 424/439; 426/648

(58) Field of Classification Search
USPC .......................... 424/400, 439; 514/549, 560
See application file for complete search history.

(56) References Cited

U.S. PATENT DOCUMENTS

| 5,198,250 | A | 3/1993 | Brillhart et al. |
| 6,461,662 | B2 | 10/2002 | Cain et al. |
| 2001/0005519 | A1 | 6/2001 | Cain et al. |
| 2006/0088574 | A1* | 4/2006 | Manning et al. ............... 424/439 |
| 2008/0306037 | A1 | 12/2008 | Medina Montano |
| 2009/0221677 | A1* | 9/2009 | Ntambi et al. ............... 514/44 A |
| 2010/0113387 | A1 | 5/2010 | Loftsson et al. |
| 2011/0213032 | A1 | 9/2011 | Cao et al. |

FOREIGN PATENT DOCUMENTS

| CN | 101278743 (A) | * | 8/2008 |
| WO | WO-2010/028336 | | 3/2010 |

OTHER PUBLICATIONS

Machine English Translation of CN 101278743 (A) (description) (Oct. 8, 2008).*
Palmitolieic acid synonyms (MSDS of palmitoleic acid provided by Cayman Chemical Company (2010)).*
Young, "The chemical & physical properties of crude fish oils for refiners & hydrogenators", Fish Oil Bulletin No. 18, published in Jun. 1986.*
Machine English Translation of CN 101278743 (A) (claims) (Oct. 8, 2008).*
Alan R. Saltiel, "Fishing Out a Sensor for Anti-inflammatory Oils," Cell 142, Sep. 3, 2010 (3 pages).
H. Kanda, et al., "MCP-1 contributes to macrophage infiltration into adipose tissue, insulin resistance, and hepatic steatosis in obesity", J Clin Invest. 2006;116(6):1494-1505.

(Continued)

*Primary Examiner* — Ernst Arnold
*Assistant Examiner* — Kyung Sook Chang
(74) *Attorney, Agent, or Firm* — Foley & Lardner LLP; Michel Morency

(57) ABSTRACT

One embodiment described herein is related to methods and compositions, such as nutraceutical formulations and dietary supplements, comprising C16:1n7-palmitoleate or derivatives thereof. The methods and compositions comprising C16:1n7-palmitoleate, or derivatives thereof, safely and effectively prevent or mitigate manifestations of cardiovascular disease, including coronary artery disease and the accumulation of cholesterol or lipid deposits in the blood vessels of a subject.

20 Claims, 4 Drawing Sheets

(56) References Cited

OTHER PUBLICATIONS

Andreas Schaeffler, et al. "Fatty acid-induced induction of Toll-like receptor-4/nuclear factor-kB pathway in adipocytes links nutritional signaling with innate immunity", Immunology 126, 233-245 (2008).
Anna Pensalfini, et al. "Protective effect of new S-acylglutathione derivatives against amyloid-induced oxidative stress," Free Radical Biology & Medicine 44 (2008)1624-1636.
D. Mozaffarian et al., "Summaries for Patients: Dietary *Trans*-Palmitoleic Acid and Diabetes," Annals of Internal Medicine, 2010 (1 page).
Darlush Mozaffarian et al., "*Trans*-Palmitoleic Acid, Metabolic Risk Factors, and New-Onset Diabetes in U.S. Adults," Annals of Internal Medicine, 153(12) 790-799 (Dec. 21, 2010).
Focus Online, "News from Garvard Medical, Dental, and Public Health Schools: Fat Finds Its Voice," Oct. 24, 2008, retrieved from: http://archives.focus.hms.harvard.edu/2008/102408/research_briefs.shtml.
Haiming Cao, et al., "Identification of a Lipokine, a Lipid Hormone Linking Adipose Tissue to Systemic Metabolisim," Cell 134, 933-944, Sep. 19, 2008.
International Search Report and Written Opinion for PCT International Application No. PCT/US2012/027489 dated Jun. 8, 2012.
J. David Curb, et al., "Serum Lipid Effects of a High-Monounsaturated Fat Diet Based on Macadamia Nuts," Arch Intern Med. 2000;160:1154-1158.
K. Maedler et al. "Distinct Effects of Saturated and Monounsaturated Fatty Acids on B-Cell Turnover and Function," Diabetes, vol. 50, 69-76, Jan. 2001.
Kelly Casós et al. "Atherosclerosis prevention by a fish oil-rich diet in apoE—/— mice is associated with a reduction of endothelial adhesion molecules." Atherosclerosis 201 (2008) 306-317.
Masako Oda, et al. "Inhibition of telomerase by linear-chain fatty acids: A Structural Analysis," Biochem. J. (2002) 367, 329-334.
Nikolaos Dimopoulos et al., "Differential effects of palmitate and palmitoleate on insulin action and glucose utilization in rat L6 skeletal muscle cells," Biochem. J. (2006) 399, 473-481.
Norbert Stefan, et al. "Circulating Palmitoleate Strongly and Independently Predicts Insulin Sensitivity in Humans," Diabetes Care; Feb. 2010, 33, 2 (405-407).
Sue Hughes, "MCP-1 a new marker of risk and therapeutic target" Copyright 1999-2012, the heart.org retrieved from: http://m.theheart.org/article/828651.doc.

\* cited by examiner

COMPOSITIONS AND METHODS COMPRISING C16:1N7-PALMITOLEATE

RELATED APPLICATION

The present application claims priority under 35 U.S.C. §119(e) to U.S. provisional patent application U.S. Ser. No. 61/449,015, filed Mar. 3, 2011, which is incorporated herein by reference.

FIELD

One embodiment described herein is related to methods and compositions, such as nutraceutical formulations and dietary supplements, comprising C16:1n7-palmitoleate or derivatives thereof. The methods and compositions safely and effectively prevent, mitigate, or reverse manifestations of cardiovascular disease, including coronary artery disease and the accumulation of cholesterol or lipid deposits in the blood vessels of a subject.

BACKGROUND

Cardiovascular disease is a global health problem. According to the Texas Heart Institute, cardiovascular disease causes 17.5 million deaths in the world each year and half of all deaths in the U.S.A. Over 80 million Americans suffer and approximately 2,400 will die each day from cardiovascular disease. Coronary artery disease (CAD), the most common form of cardiovascular disease, is the leading cause of death in America today. Coronary artery disease is usually caused by vascular stenosis, or the narrowing of the arterial lumen, thereby reducing or totally blocking the blood supply to the heart muscles. Stenosis begins in the intima of the artery with the deposition of fatty debris from blood. Smooth muscle cells from the internal elastic membrane and media proliferate into the intima. Collagen and elastin produced from these cells accumulate resulting in a fibrous plaque. As the process continues, cholesterol rich material and necrotic cells accumulating in the plaque cause it to encroach upon the arterial lumen. Eventually, the plaque calcifies and hardens. The narrowed lumen of the artery does not permit adequate blood flow causing that portion of the myocardium to become ischemic. An advanced plaque may rupture or platelets may aggregate at the site to produce an intravascular blood clot or thrombus. A sudden critical reduction in blood supply to the myocardium, usually because of plaque rupture and/or thrombosis, leads to acute myocardial infarction.

Cardiovascular diseases, such as coronary artery disease, develop over extended periods that may span years. There exists a substantial need for agents that are safe enough for continuous administration over such long periods of time (e.g., as a prophylactic), but that are also sufficiently effective to diminish, prevent, or reverse the acute symptoms of cardiovascular diseases, such as coronary artery disease and the accumulation of cholesterol or lipid deposits in the blood vessels of a subject.

SUMMARY

One embodiment described herein is related to methods and compositions, such as nutraceutical formulations and dietary supplements, comprising C16:1n7-palmitoleate and derivatives thereof, that are highly safe and unexpectedly effective for the prevention or mitigation of cardiovascular diseases such as coronary artery disease. In certain embodiments, compositions comprising C16:1n7-palmitoleate or derivatives thereof are provided for the prevention or mitigation of cholesterol or lipid deposits in the blood vessel of a subject.

It has been surprisingly found that compositions having a significant wt % (i.e., greater than 20 wt %) of C16:1n7-palmitoleate, and derivatives thereof, can be used to effectively alter the blood lipid profile in a subject, for example, by increasing the ratio of high-density lipoprotein (HDL) relative to low-density lipoprotein (LDL) in the patient's blood plasma.

Compositions having greater than 20 wt % of C16:1n7-palmitoleate have generally evaded study, in part, because C16:1n7-palmitoleate is difficult to purify and, if purified, becomes relatively unstable. Substantially pure (99%) C16:1n7-palmitoleic acid is sold in ampules by Sigma-Aldrich® for over $200/gram. Despite being under an inert atmosphere, the ampules of C16:1n7-palmitoleic acid have expiration dates due to their limited shelf-life. Likewise, methyl C16:1n7-palmitoleate (99%) also has a limited shelf-life and is sold by Fluka® for over $90/gram. Thus, substantially pure C16:1n7-palmitoleic derivatives are expensive and relatively unstable.

Less concentrated sources of C16:1n7-palmitoleate with extended shelf lives are found in natural oils. For example, C16:1n7-palmitoleate is a constituent (approximately 20 wt %) of *macadamia* nut oil and sea buckthorn. Both of these expensive sources have approximately 80 wt % of other components that help to stabilize the C16:1n7-palmitoleate, but which necessarily dilute or counteract the capacity of C16:1n7-palmitoleate to prevent or mitigate cardiovascular disease. For example, *macadamia* nut oil and sea buckthorn have approximately 65 wt % and 24 wt %, respectively, of C18:1n9-oleate, which can dilute the effect of C16:1n7-palmitoleate. C18:1n9-Oleate and C16:1n7-palmitoleate are monounsaturated fatty acids that are difficult to separate.

Further, *macadamia* nut oil and sea buckthorn contain significant quantities of unhealthy saturated fatty acids that might counteract the capacity of C16:1n7-palmitoleate to prevent or mitigate cardiovascular disease. In particular, sea buckthorn contains approximately 22 wt % of saturated C16:0-palmitate. According to published guidelines by the American Heart Association (AHA) and, in particular, a 2003 World Health Organization (WHO) expert consultation report, the "intake of saturated fatty acids, such as myristic acid (C14:0), palmitic acid (C16:0), and stearic acid (C18:0), is directly related to cardiovascular risk." The report suggests that the intake of saturated fatty acids be restricted to less than 10% and, ideally, less than 7% of dietary intake. Thus, the cardiovascular benefits of natural oils having C16:1n7-palmitoleate may be mitigated, in part, to the presence of saturated fatty acid co-metabolites in these oils.

Thus, as noted above, in one aspect is provided methods to prevent or mitigate cardiovascular disease with compositions comprising C16:1n7-palmitoleate and derivatives thereof, wherein, unlike natural oils, the wt % of the C16:1n7-palmitoleate derivative exceeds the wt % of any other single ingredient in the composition. Surprisingly, compositions derived from natural oils, such as *macadamia* nut oil, having approximately 20 wt % C16:1n7-palmitoleate were found to mitigate cardiovascular disease. Accordingly, methods were developed to further refine and fractionate natural oils into compositions comprising greater than 20 wt % of a C16:1n7-palmitoleate derivative, wherein the wt % of the C16:1n7-palmitoleate derivative exceeds the wt % of any other single ingredient in the composition. This was particularly challenging because natural oils having C16:1n7-palmitoleate also contain saturated fatty acids, such as C16:0-palmitate, monounsaturated fatty acids, such as C18:1n9-oleate, and additional polyunsaturated fatty acids that are chemically similar to C16:1n7-palmitoleate but must be reduced in concentration relative to C16:1n7-palmitoleate until the wt % of the C16:1n7-palmitoleate derivative exceeds the wt % of any other single ingredient in the composition.

In some embodiments, a dietary supplement is provided comprising a C16:1n7-palmitoleate derivative, wherein the wt % of the C16:1n7-palmitoleate derivative exceeds the wt % of any other single ingredient in the dietary supplement. In other embodiments, a dietary supplement is provided comprising a C16:1n7-palmitoleate derivative, wherein the wt % of the C16:1n7-palmitoleate derivative exceeds the wt % of any other single ingredient in the dietary supplement, and wherein the composition comprises additional fatty acids that extend the shelf-life of the composition.

In certain embodiments, the C16:1n7-palmitoleate moiety of the C16:1n7-palmitoleate derivative is obtained from a source selected from the group consisting of fish, *macadamia* nuts, sea buckthorn, tallow, algae, bacteria, yeast, or a combination thereof. In other embodiments, the C16:1n7-palmitoleate moiety of the C16:1n7-palmitoleate derivative is obtained from fish. In some embodiments, the fish are selected from the group consisting of anchovies, menhaden, pollock, herring, cod, salmon, smelt, tuna, mackerel, krill, or a combination thereof. In one embodiment, the fish are anchovies. In another embodiment, the fish are menhaden.

In some embodiments, the dietary supplement comprises from about 30 wt % to about 90 wt % of the C16:1n7-palmitoleate derivative. In other embodiments, the dietary supplement comprises from about 30 wt % to about 90 wt % of the C16:1n7-palmitoleate derivative. In some embodiments, the dietary supplement comprises from about 35% to about 60 wt % of the C16:1n7-palmitoleate derivative. In other embodiments, the dietary supplement comprises about 35% of the C16:1n7-palmitoleate derivative. In other embodiments, the dietary supplement comprises about 45% of the C16:1n7-palmitoleate derivative. In other embodiments, the dietary supplement comprises about 50% of the C16:1n7-palmitoleate derivative. In other embodiments, the dietary supplement comprises about 60% of the C16:1n7-palmitoleate derivative. In each of the above embodiments, the dietary supplement may further comprise additional fatty acids that extend the shelf-life of the dietary supplement.

In some embodiments, the dietary supplement comprises a reduced wt % of unhealthy saturated fatty acids that might counteract the capacity of C16:1n7-palmitoleate to prevent or mitigate cardiovascular disease. For example, in some embodiments, the dietary supplement comprises a palmitate derivative, wherein the ratio of the C16:1n7-palmitoleate derivative to the palmitate derivative (i.e., palmitoleate:palmitate) is from about 2:1 to about 50:1. In other embodiments, the ratio of the C16:1n7-palmitoleate derivative to the palmitate derivative (i.e., palmitoleate:palmitate) is from about 5:1 to about 15:1 In some embodiments, the ratio of the C16:1n7-palmitoleate derivative to the palmitate derivative (i.e., palmitoleate:palmitate) is from about 10:1 to about 20:1. In other embodiments, the ratio of the C16:1n7-palmitoleate derivative to the palmitate derivative (i.e., palmitoleate:palmitate) is about 10:1. In some embodiments, the ratio of the C16:1n7-palmitoleate derivative to the palmitate derivative (i.e., palmitoleate:palmitate) is from about 20:1 to about 50:1.

In certain embodiments, the dietary supplement comprises a reduced wt % of other unsaturated fatty acids that might dilute the capacity of C16:1n7-palmitoleate to prevent or mitigate cardiovascular disease. For example, in some embodiments, the dietary supplement comprises an oleate derivative, wherein the wt % of C16:1n7-palmitoleate exceeds the wt % of the oleate derivative. In some embodiments, the ratio of the C16:1n7-palmitoleate derivative to the oleate derivative (i.e., palmitoleate:oleate) is from about 1.1:1 to about 50:1. In some embodiments, the ratio of the C16:1n7-palmitoleate derivative to the oleate derivative (i.e., palmitoleate:oleate) is from about 1.1:1 to about 2:1.

In some embodiments, the C16:1n7-palmitoleate derivative is a cis-C16:1n7-palmitoleate derivative selected from the group consisting of the free acid, salt, $(C_1-C_4)$alkyl ester, monoglyceride, diglyceride, triglyceride, or a combination thereof. In some embodiments, the cis-C16:1n7-palmitoleate derivative is the ethyl ester.

In another aspect, a method for treating or preventing a cardiovascular disease or condition in a subject is provided comprising the administration of a dietary supplement of any one of the embodiments described above.

In certain embodiments, the method further comprises altering the blood lipid profile in a subject. In other embodiments, the method further comprises preventing or reducing the deposition of cholesterol in a blood vessel in the subject. In certain embodiments, the lumen diameter of at least one blood vessel in the subject is increased by at least 10%. In other embodiments, the lumen diameter of at least one blood vessel in the subject is increased by at least 50%. In certain embodiments, the method further comprises preventing or reducing a cholesterol-associated lesion in a blood vessel in the subject. In other embodiments, the method further comprises increasing the ratio of high-density lipoprotein (HDL) relative to low-density lipoprotein (LDL) in the blood serum of the subject. In certain embodiments, the method further comprises increasing the ratio of apolipoprotein A1 (Apo-A1) relative to apolipoprotein B (Apo-B) in the blood serum of the subject. In other embodiments, the method further comprises reducing blood pressure or preventing an increase in blood pressure in the subject. In certain embodiments, the subject exhibits at least a 10 mmHg reduction in systolic blood pressure. In other embodiments, the subject exhibits at least a 20 mmHg reduction in systolic blood pressure. In certain embodiments, the method further comprises preventing or reducing stenosis in a subject, or preventing or reducing restenosis in a subject following angioplasty.

In certain embodiments, the method further comprises the administration of a medication selected from the group consisting of an angiotensin-converting enzyme inhibitor (e.g., benazepril, fosinopril, lisinopril, quinapril), angiotensin receptor blocker, (e.g., losartan), beta-blocker, (e.g., metoprolol tartrate, betaxolol, valsartan), diuretic (e.g., hydrochlorothiazide), vasodilator (e.g., isosorbide dinitrate), α-blocker, calcium channel blocker, a HMG-CoA reductase inhibitor (e.g., a statin, such as rosuvastatin (Crestor®), lovastatin (Mevacor®), cerivastatin (Baycol®), fluvastatin (Lescol®), simvastatin (Zocor®), pravastatin (Pravachol®) and atorvastatin (Lipitor®)), a fibrate (e.g., clofibrate (Atromid-S®)), a bile acid sequestrant (e.g., cholestyramine and colestipol (Colestid®), and nicotinic acid (niacin)), gemfibrozil (Lopid® and Gemcor®), ezetimibe therapy, and probucol (Panavir®). In one embodiment, the medication is a HMG-CoA reductase inhibitor.

DETAILED DESCRIPTION

Definitions

Figure 1A:
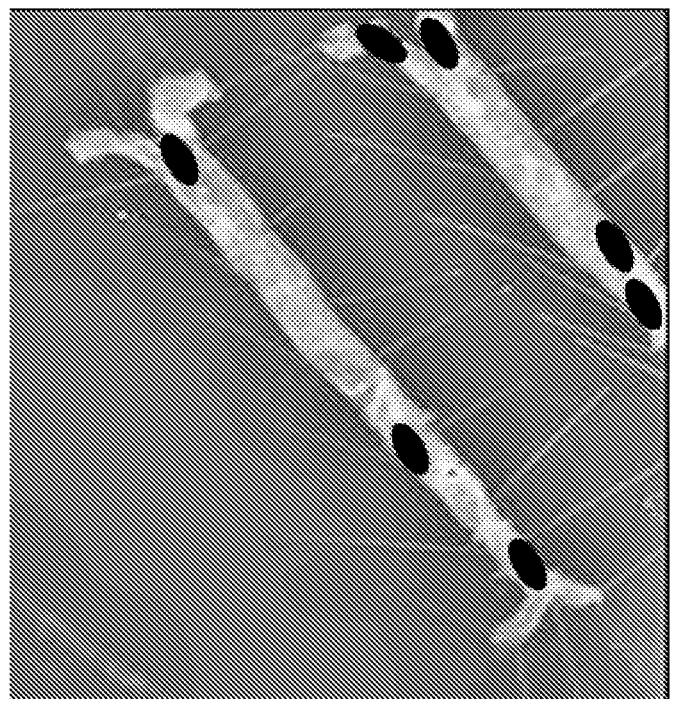
FIG. 1A illustrates the presence of significant cholesterol-derived plaques in the aorta of Apo-E knockout mice from the control treatment group that was fed a Western diet. The cholesterol-derived plaques were visualized by Sudan IV staining (The originally stained areas have been shaded with black ovals to improve visibility.)

As used herein, the term "plaque" refers to the deposition of lipids and/or cholesterol in a blood vessel.

As used herein, the term "approximately" or "about" in reference to a number are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value).

As used herein, the term "subject" refers to a mammal, including but not limited to a dog, cat, horse, cow, pig, sheep, goat, chicken, rodent, or primate. Subjects can be house pets (e.g., dogs, cats), agricultural stock animals (e.g., cows, horses, pigs, chickens, etc.), laboratory animals (e.g., mice, rats, rabbits, etc.), but are not so limited. Subjects include human subjects. The human subject may be a pediatric, adult, or a geriatric subject. The human subject may be of either sex.

As used herein, the term "monoglyceride" refers to a fatty acid chain, such as C16:1n7-palmitoleate, covalently bonded to a glycerol molecule through an ester linkage. As used herein, the term "diglyceride" refers to a fatty acid chain, such as C16:1n7-palmitoleate, covalently bonded to a glycerol molecule through an ester linkage, wherein the glycerol molecule is further bonded to one additional fatty acid chain, which may or may not be C16:1n7-palmitoleate, though one additional ester linkage. As used herein, the term "triglyceride" refers to a fatty acid chain, such as C16:1n7-palmitoleate, covalently bonded to a glycerol molecule through an ester linkage, wherein the glycerol molecule is further bonded to two additional fatty acid chains, either or both of which may or may not be C16:1n7-palmitoleate, though two additional ester linkages.

As used herein, the term "composition" includes therapeutic and dietary formulations including, but not limited to a dietary supplement, nutraceutical formulation, or pharmaceutical formulation. Further, the terms composition, dietary supplement, nutraceutical formulation, and pharmaceutical formulation are used interchangeably herein.

As used herein, the terms "cardiovascular disease" and "cardiovascular condition" include disorders of the heart and vasculature, including, for example, atherosclerosis, transient ischemic attack, systolic dysfunction, diastolic dysfunction, aneurysm, aortic dissection, myocardial ischemia, acute myocardial infarction (AMI), acute ST-segment elevation myocardial infarction (STEMI), acute non-ST-segment elevation myocardial infarction (NSTEMI), angina pectoris, unstable angina (UA), and stable angina (SA), myocardial infarction, congestive heart failure, dilated congestive cardiomyopathy, hypertrophic cardiomyopathy, restrictive cardiomyopathy, cor pulmonale, arrhythmia, valvular heart disease, endocarditis, pulmonary embolism, venous thrombosis, peripheral vascular disease, and peripheral artery disease.

As used herein, the term "blood vessel" includes arteries, veins, and capillaries. By "coronary blood vessel" is meant a blood vessel that delivers blood to the heart or transports blood away from the heart. Exemplary coronary blood vessels include (without limitation) the aorta, the right and left coronary arteries, the pulmonary vein, the pulmonary artery, the circumflex artery, the left anterior descending artery, and the vena cava.

As used herein, the terms "angioplasty" or "percutaneous transluminal angioplasty (PTA)" include any percutaneous transluminal method of decreasing stenosis within a blood vessel, whether caused by the existence of an atheromatous plaque, thrombosis, embolus, and/or mineral deposit, by any of a number of means such as balloon dilation, thermal ablation, laser atherectomy, mechanical shaving, extraction, or ultrasonic pulverization. Examples include coronary angioplasty, also known as PTCA, and angioplasty used to treat peripheral vascular disease such as femoropopliteal angioplasty.

As used herein, the term "biomarker related to a cardiovascular condition" includes a biomarker that is known in the art to be derived from cardiac tissue and that is elevated in the circulation of subjects suffering from a cardiovascular condition. Exemplary biomarkers of a cardiovascular condition include, without limitation, annexin V, β-enolase, cardiac troponin I, cardiac troponin T, creatine kinase-MB, glycogen phosphorylase-BB, heart-type fatty acid binding protein, C-reactive protein, growth differentiation factor 15, phosphoglyceric acid mutase-MB, S-100ao, myoglobin, actin, myosin, and lactate dehydrogenase, or markers related thereto. See, e.g., Scirica, J. Am. Coll. Cardiol. 55:1403-1415, 2010.

As used herein, the term "stenosis" includes a pathologic narrowing of a blood vessel.

As used herein, the terms "reocclusion" or "restenosis" include the reoccurrence of stenosis (i.e., narrowing) of a blood vessel, leading to restricted blood flow. For example, reocclusion may pertain to a blocked or narrowed artery that has been treated to clear the blockage or occlusion and that has subsequently become reoccluded. Reocclusion is defined as a reduction in the circumference of the lumen of the blood vessel by, e.g., from about 5% to about 10%, from about 10% to about 20%, from about 20% to about 30%, from about 30% to about 50%, from about 50% to about 75%, or from about 75% to about 100%. Alternatively, reocclusion may refer to stenosis that results in reduced organ perfusion. Reocclusion may occur in a subject with, e.g., a cardiovascular condition.

As used herein, the term "thrombosis" includes the formation or presence of a clot in the cardiovascular system that may be occlusive or attached to the vessel without obstructing the lumen.

As used herein, the term "effective amount" includes an amount sufficient to prevent or ameliorate a manifestation of cardiovascular disease, such as cholesterol deposition, vascular stenosis, or restenosis following angioplasty. It will be appreciated that there will be many ways known in the art to determine the effective amount for a given application. For example, the pharmacological methods for dosage determination may be used in the therapeutic context.

Methods to Prevent or Mitigate the Deposition of Cholesterol in Blood Vessels

It has been found that compositions, such as nutraceutical formulations and dietary supplements, comprising C16:1n7-palmitoleate or one or more derivatives thereof, are surprisingly useful to prevent, diminish, or reverse one or more manifestations of a cardiovascular disease.

In one aspect, a method for treating or preventing a cardiovascular disease or condition in a subject is provided comprising the administration of a composition, such as nutraceutical formulations or dietary supplement, comprising C16:1n7-palmitoleate or one or more derivatives thereof. In some embodiments, the cardiovascular disease is selected from the group consisting of an acute coronary syndrome, atherosclerosis, transient ischemic attack, systolic dysfunction, diastolic dysfunction, aneurysm, aortic dissection, myocardial ischemia, angina pectoris, stable angina, unstable angina, acute myocardial infarction, acute ST-segment elevation myocardial infarction (STEMI), acute non-STEMI, congestive heart failure, dilated congestive cardiomyopathy, hypertrophic cardiomyopathy, restrictive cardiomyopathy, cor pulmonale, arrhythmia, valvular heart disease, endocarditis, pulmonary embolism, venous thrombosis, and peripheral vascular disease.

In some embodiments, methods and compositions are provided, such as nutraceutical formulations and dietary supplements, comprising C16:1n7-palmitoleate or one or more derivatives thereof, are useful to prevent, diminish, or reverse one or more manifestations of coronary artery disease. Coronary artery disease is the most common form of cardiovascular disease and is usually caused by vascular stenosis, the partial or nearly complete blocking of a blood vessel, also called an occlusion of a blood vessel. Stenosis typically results from the build-up of plaques comprising lipids such as cholesterol within a blood vessel. Although stenosis can occur in any of the blood vessels within a person's body, a particular concern is stenosis within the coronary and carotid blood vessels. For example, a stenosis of a coronary artery can result in a reduction of the blood flow to the heart muscle, possibly resulting in angina or a heart attack.

In further embodiments, methods and compositions are provided, such as nutraceutical formulations and dietary supplements, comprising C16:1n7-palmitoleate or one or more derivatives thereof that are surprisingly useful for preventing or reducing the deposition of cholesterol-containing plaque within the body of a subject. The methods typically involve an oral administration of a nutraceutical formulation or dietary supplement, comprising C16:1n7-palmitoleate or one or more derivatives thereof. In further embodiments, methods are provided to prevent or reduce the deposition of cholesterol in one or more blood vessels in a subject, wherein the blood vessel is selected from the group consisting of an artery, a vein, and a capillary. In some embodiments, methods and compositions are provided, such as nutraceutical formulations and dietary supplements, comprising C16:1n7-palmitoleate or one or more derivatives thereof are particularly useful to prevent, diminish, or reverse the accumulation of plaques comprising lipids such as cholesterol within a blood vessel of a subject. In certain embodiments, the lumen diameter of at least one blood vessel in the subject is increased by at least 10%. In other embodiments, the lumen diameter of at least one blood vessel in the subject is increased by at least 50%. In still further embodiments, methods are provided to prevent or reduce a cholesterol-associated lesion in a blood vessel in a subject, wherein the cholesterol-associated lesion is selected from the group consisting of an initial lesion, fatty streak, intermediate lesion, atheroma, fibroatheroma, and a complicated lesion. In certain embodiments, the method further comprises preventing or reducing a cholesterol-associated lesion in a blood vessel in the subject. In other embodiments, the method further comprises increasing the ratio of high-density lipoprotein (HDL) relative to low-density lipoprotein (LDL) in the blood serum of the subject. In certain embodiments, the method further comprises increasing the ratio of apolipoprotein A1 (Apo-A1) relative to apolipoprotein B (Apo-B) in the blood serum of the subject.

In further embodiments, a method is provided of administering or providing a composition, such as a nutraceutical formulation or a dietary supplement, comprising C16:1n7-palmitoleate or one or more derivatives thereof, for preventing or reducing the deposition of deposits or plaques comprising cholesterol in a blood vessel in a subject. In certain embodiments, the dietary supplements reduce the deposition of plaque in a blood vessel in a subject from about 1% to about 10%, or from about 10% to about 25%, or from about 25% to about 50%, or from about 50% to about 75%, or from about 75% to about 99%.

Human patients treated with the methods and compositions described herein, such as a nutraceutical formulation or a dietary supplement, comprising C16:1n7-palmitoleate or one or more derivatives thereof, may be followed by a physician to track the success of the methods and/or composition. In further embodiments, methods are provided to measure the extent to which the compositions, such as nutraceutical formulations and dietary supplements, comprising C16:1n7-palmitoleate or one or more derivatives thereof prevent, diminish, or reverse the deposition of plaque in a blood vessel in a subject. Various methods exist for detecting and measuring such plaques or stenosis. One way of detecting stenosis is an angiogram. An angiogram requires inserting a catheter into a blood vessel and releasing a radiocontrast agent (such as iodine) into the bloodstream. In the presence of the radiocontrast agent, the blood vessel is viewed with an x-ray machine. The radiocontrast agent within the blood allows the inner surface of the blood vessel to be visible on the x-ray image. This procedure allows accurate determination of whether stenosis is present. Alternatively, a computerized tomography (CT) scan, that takes image slices of arteries can be used to measure the effectiveness of the compositions, such as a nutraceutical formulation or a dietary supplement, comprising C16:1n7-palmitoleate or one or more derivatives thereof.

As used herein, the "prevention," "reduction," and "reversal" of plaques or stenosis by the methods and compositions described herein, such as nutraceutical formulations and dietary supplements, comprising C16:1n7-palmitoleate or one or more derivatives thereof, imply a reduction in the narrowing of the vessel lumen diameter such that the blood flow does not fall below values considered to be normal for the specific vessel. Clinicians or practitioners skilled in the art will be familiar with the normal values for blood flow for a specific vessel. As used herein "prevention," "reduction," and "reversal" can also be used in reference to neointimal hyperplasia and includes any decrease of 20% or greater (50% or greater, or 75% or greater) in the proliferation rate or overall number of vascular smooth muscle cells. As used herein "prevention," "reduction," and "reversal" by the methods and compositions described herein, such as nutraceutical formulations and dietary supplements, comprising C16:1n7-palmitoleate or one or more derivatives thereof, can also mean a reduction in the narrowing of the vessel lumen diameter such that the diameter of the lumen after treatment is 0 to 25%, 25 to 50%, or 50% or more than the diameter of the lumen before treatment.

In some embodiments, a coronary angiography is used to determine lumen diameter of the treated vessel. An increase of 5%, 10%, 15%, 20%, 25%, 30%, 35%, 40%, 45% or more, 50%, 55%, 60%, 65%, 70% or more, or 75%, 80%, 85%, 90%, 95% or more in lumen diameter post treatment as compared to pre-treatment is indicative of therapeutic efficacy. The diameter of the treated vessel can also be compared to a reference distal and proximal segment to determine therapeutic efficacy. Additional methods for measuring therapeutic efficacy include magnetic resonance angiography. In some embodiments, the patient is monitored in the short-term (up to six months after initial treatment) or the long-term (six months or more after the initial treatment) to determine the efficacy of the treatment using the compositions described herein.

Accordingly, in some embodiments, administration of the methods and compositions described herein, such as nutraceutical formulations and dietary supplements, comprising C16:1n7-palmitoleate or one or more derivatives thereof, prevents the formation of plaques or stenosis in a blood vessel as determined from one or more angiograms. In further embodiments, administration of the compositions reduces the formation of plaques or stenosis in a blood vessel as determined from one or more angiograms. In still further embodiments, administration of the compositions reduces the formation of plaques or stenosis in a blood vessel as determined from one or more angiograms, wherein the reduction is from about 1% to about 10%, or from about 10% to about 25%, or from about 25% to about 50%, or from about 50% to about 75%, or from about 75% to about 99%.

Additional methods for measuring therapeutic efficacy include intravascular ultrasound (IVUS), which allows for quantitation of neointimal formation, luminal diameter, plaque area and volume. In further embodiments, a method is provided for detecting stenosis that relies on a microphone, accelerometer, or other transducer that is positioned on the patient's skin to sense cardiac sounds. It is generally known that blood flowing through an occluded or partially occluded vessel tends to transition from laminar flow to turbulent flow as it travels into, through, and past a restriction. It is also known that turbulent blood flow tends to generate an acoustic wave that propagates through the patient's body tissue and can be sensed at the patient's skin. These acoustic waves have very low sound pressure levels (on the order of −100 dB) and also occur across an extended frequency range that includes moderately high frequencies (up to about 1.2 kHz). These acoustic waves tend to be attenuated by the body tissue, particularly at higher frequencies, and therefore require transducers having very high sensitivity to measure. However, such transducers do exist and can be used successfully to detect stenosis. For example, see Padmanabhan et al., *Accelerometer Type Cardiac Transducer for Detection of Low Level Heart Sounds*, IEEE Transactions on Biomedical Engineering, Vol. 40, No. 1, January 1993. In further embodiments, a doppler ultrasound, an ankle-brachial index, or an electrocardiogram (ECG) will be administered to measure the efficacy of the methods and compositions. Doppler ultrasound utilizes a special probe to measure the blockage and speed of blood flow in one or more arteries Ankle-brachial index determines the blood pressure in the ankle and arm to determine if there is plaque in the arteries of legs and feet of a subject. An ECG enables the detection any abnormal rhythms in the heart and therefore, any potential blockages in the heart's arteries.

Accordingly, in some embodiments, administration of the methods and compositions described herein, such as nutraceutical formulations and dietary supplements, comprising C16:1n7-palmitoleate or one or more derivatives thereof prevents the formation of plaques or stenosis in a blood vessel as determined from data obtained from a microphone, accelerometer, or other transducer. In further embodiments, administration of the methods and/or compositions reduces the formation of plaques or stenosis in a blood vessel as determined from data obtained from a microphone, accelerometer, or other transducer. In still further embodiments, administration of the methods and/or compositions reduces the formation of plaques or stenosis in a blood vessel as determined from data obtained from a microphone, accelerometer, or other transducer, wherein the reduction is from about 1% to about 10%, or from about 10% to about 25%, or from about 25% to about 50%, or from about 50% to about 75%, or from about 75% to about 99%.

Methods to Prevent or Mitigate the Deposition of Cholesterol Following Angioplasty Treatment of a stenosed artery usually involves one of two options: by-pass surgery or percutaneous transluminal angioplasty (PTA), commonly known as angioplasty. Although effective in providing an alternate route for blood flow, by-pass surgery is a high-risk and high-cost procedure. In contrast, angioplasty is a safer, less intrusive, and less expensive method of treatment.

Angioplasty has proven to be a successful method of treatment for opening the blocked, or stenosed, vessel and restoring blood flow. However, it has been found that restenosis, or re-narrowing of the vessel lumen, frequently occurs. In the case of coronary angioplasty, restenosis occurs in approximately 20-50% of cases within six months of the procedure. There is no known cure available for the treatment of this costly limitation of angioplasty therapy.

In some embodiments, methods and compositions are provided, such as nutraceutical formulations and dietary supplements, comprising C16:1n7-palmitoleate or one or more derivatives thereof to prevent, diminish, or reverse vascular stenosis or restenosis associated with angioplasty by administering a combination comprising C16:1n7-palmitoleate or one or more derivatives thereof. In some embodiments, methods and compositions are provided, such as nutraceutical formulations and dietary supplements, comprising C16:1n7-palmitoleate or one or more derivatives thereof for the prevention, reduction, reversal, or treatment of stenosis or restenosis, wherein said stenosis or restenosis is characterized by the deposition of extracellular matrix comprising cholesterol. In further embodiments, methods and compositions are provided, such as nutraceutical formulations and dietary supplements, comprising C16:1n7-palmitoleate or one or more derivatives thereof for the prevention, reduction, reversal, or treatment of stenosis prior to an angioplasty procedure and the surgical introduction of a stent. In further embodiments, methods and compositions are provided, such as nutraceutical formulations and dietary supplements, comprising C16:1n7-palmitoleate or one or more derivatives thereof for the reduction, reversal, or treatment of restenosis following an angioplasty procedure and the surgical introduction of a stent.

Methods to Prevent or Mitigate High Blood Pressure

In some embodiments, methods and compositions are provided, such as nutraceutical formulations and dietary supplements, comprising C16:1n7-palmitoleate or one or more derivatives thereof for reducing blood pressure or preventing an increase in blood pressure and for treating or preventing hypertension or prehypertension in a subject.

Generally, a subject may be considered prehypertensive upon consecutive readings at two or more occasions with a systolic pressure of from 120 to 139 mmHg or a diastolic pressure of from 80 to 89 mmHg. A subject may be considered hypertensive upon consecutive readings at two or more occasions with systolic/diastolic pressure greater than or equal to 140/90 mmHg.

Individuals having elevated blood pressure or hypertension are at a significantly greater risk for developing numerous disorders and complications. The extent and severity of these disorders and complications suggest an urgent need for early and effective treatment strategies that reduce blood pressure and that treat hypertension or prevent/reverse the progression of hypertension. Relatively minor reductions in blood pressure can significantly reduce the co-morbidities and co-mortalities associated with hypertension. For example, in adults aged 40-69, a 20 mmHg reduction in systolic blood pressure (approximately equivalent to a 10 mmHg reduction in diastolic blood pressure) was associated with a greater than twofold reduction in death due to stroke and other vascular diseases. (Lewington et al. (2002) Lancet 360:1903-1913.) Individuals with elevated blood pressure, including hypertensive and prehypertensive subjects, are a heterogeneous population. This is due, in part, to the multifactorial etiology and numerous underlying mechanisms associated with elevated blood pressure. (Welsh et al. (2004) Int J Clin Pract. 58:956-63.) For example, elevated blood pressure may be caused by other underlying diseases such as chronic kidney disease or cardiovascular disease. The heterogeneity of these patient populations results in a varied response to antihypertensive therapy. (Laragh et al. Hypertension 12:223-226.)

Therefore, there exists a need for methods and compositions effective for reducing blood pressure and for treating hypertension and prehypertension. These needs are addressed and met by providing the novel methods and compositions, such as nutraceutical formulations and dietary supplements, comprising C16:1n7-palmitoleate or one or more derivatives thereof for use in reducing blood pressure and in treating or preventing hypertension or prehypertension in subjects, including subjects having cardiovascular disease. Such methods and compositions can be used alone or in combination with current therapies to reduce blood pressure and treat hypertension or prehypertension in subjects in need thereof.

The mean arterial pressure (MAP) represents a notional average blood pressure in a subject. MAP is defined as the average arterial pressure during a single cardiac cycle. Mean arterial pressure can be determined according to any method accepted and utilized by those skilled in the art. For example, mean arterial pressure can be calculated according to the following equation: (diastolic pressure+⅓[systolic pressure–diastolic pressure]). (Rogers et al. (2001) Ann Intern Med. 134:1024-32.) In one embodiment, the present methods and compositions are provided, such as nutraceutical formulations and dietary supplements, comprising C16:1n7-palmitoleate or one or more derivatives thereof for reducing mean arterial pressure in subjects having elevated or high blood pressure or hypertension.

A human subject having a systolic blood pressure of greater than about 140 mmHg or a diastolic blood pressure of greater than about 90 mmHg is considered to have hypertension. Hypertension may be further classified as mild hypertension (Stage 1, systolic blood pressure of between 140 to 159 mmHg; diastolic blood pressure of between 90 to 99 mmHg), moderate hypertension (Stage 2, systolic blood pressure of between 160 to 179 mmHg; diastolic blood pressure of between 100 to 109 mmHg), severe hypertension (Stage 3, systolic blood pressure of between 180 to 209 mmHg; diastolic blood pressure of between 110 to 119 mmHg), or very severe hypertension (Stage 4, systolic blood pressure of greater than 210 mmHg; diastolic blood pressure of greater than 120 mmHg). Thus, contemplated herein is the treatment of subjects with methods and compositions, such as nutraceutical formulations and dietary supplements, comprising C16:1n7-palmitoleate or one or more derivatives thereof to prevent hypertension including mild hypertension, moderate hypertension, severe hypertension, and very severe hypertension.

In another embodiment, upon treatment with a methods and compositions, such as nutraceutical formulations and dietary supplements, comprising C16:1n7-palmitoleate or one or more derivatives thereof, the subject or subject group exhibits a reduction in systolic blood pressure of from about 1 mmHg to about 10 mmHg, or from about 10 mmHg to about 25 mmHg, or from about 25 mmHg to about 50 mmHg, or from about 50 mmHg to about 75 mmHg, or from about 75 mmHg to about 100 mmHg.

In another embodiment, upon treatment with a methods and compositions, such as nutraceutical formulations and dietary supplements, comprising C16:1n7-palmitoleate or one or more derivatives thereof, the subject or subject group exhibits a reduction in diastolic blood pressure of from about 1 mmHg to about 5 mmHg, or from about 5 mmHg to about 10 mmHg, or from about 10 mmHg to about 20 mmHg, or from about 20 mmHg to about 30 mmHg, or from about 30 mmHg to about 40 mmHg, or from about 40 mmHg to about 50 mmHg.

In certain aspects, the subject at risk is a subject previously treated with or currently taking one or more blood pressure medications including, e.g., angiotensin-converting enzyme inhibitors (e.g., benazepril, fosinopril, lisinopril, quinapril), angiotensin receptor blockers, (e.g., losartan), beta-blockers, (e.g., metoprolol tartrate, betaxolol, valsartan), diuretics (e.g., hydrochlorothiazide), vasodilators (e.g., isosorbide dinitrate), α-blockers, calcium channel blockers, and statins.

Methods to Improve Blood Lipid Profiles

In another embodiment, methods and compositions are provided, such as nutraceutical formulations and dietary supplements, comprising C16:1n7-palmitoleate or one or more derivatives thereof for altering the blood lipid profile in a subject comprising providing or administering to a subject or subject group in need thereof a composition as described herein. In certain embodiments, the subject or subject group has hypertriglyceridemia, hypercholesterolemia, mixed dyslipidemia and/or elevated triglycerides.

Without being bound by theory, it is contemplated that compositions comprising C16:1n7-palmitoleate, or one or more derivatives thereof, have numerous health benefits that include (a) reducing plasma concentrations of LDL in a subject, (b) increasing plasma concentrations of HDL in a subject, (c) reducing the levels of cholesterol deposition within a blood vessel in a subject, and (d) reducing the incidence of lesions within a blood vessel in a subject. It is contemplated that benefits (a) through (d), though potentially related, are mechanistically separate and distinct benefits. For example, recent studies have shown that atherosclerosis can occur independently of obesity and insulin resistance. See J. Mark Brown et al., *Circulation.* 2008; 118:1467-1475.

In another embodiment, the subject or subject group being treated or provided with the methods and compositions, such as nutraceutical formulations and dietary supplements, comprising C16:1n7-palmitoleate or one or more derivatives thereof has a baseline triglyceride level (or median baseline triglyceride level in the case of a subject group), fed or fasting, of at least about 300 mg/dl, at least about 500 mg/dl, at least about 700 mg/dl, at least about 900 mg/dl, at least about 1100 mg/dl, at least about 1300 mg/dl, or at least about 1500 mg/dl.

In another embodiment, the subject or subject group being treated or provided with the methods and compositions, such as nutraceutical formulations and dietary supplements, comprising C16:1n7-palmitoleate or one or more derivatives thereof exhibits a fasting baseline absolute plasma level of free C16:1n7-palmitoleate (or mean thereof in the case of a subject group) not greater than about 0.70 nmol/ml, or not greater than about 0.50 nmol/ml, or not greater than about 0.30 nmol/ml, or not greater than about 0.10 nmol/ml, or not greater than about 0.05 nmol/ml. In another embodiment, the subject or subject group being treated in accordance with the described methods exhibits a baseline fasting plasma level (or mean thereof) of free C16:1n7-palmitoleate, expressed as a percentage of total free fatty acid, of not more than about 10%, not more than about 5%, not more than about 2%, not more than about 1%, or not more than about 0.15%. In one such embodiment, free plasma C16:1n7-palmitoleate and/or total fatty acid levels are determined prior to initiating therapy.

In another embodiment, the subject or subject group being treated or provided with the described methods and compositions, such as nutraceutical formulations and dietary supplements, comprising C16:1n7-palmitoleate or one or more derivatives thereof exhibits a fasting baseline absolute plasma level of total fatty acid (or mean thereof) not greater than about 250 nmol/ml, not greater than about 150 nmol/ml, not greater than about 100 nmol/ml, or not greater than about 50 nmol/ml.

In another embodiment, the subject or subject group being treated or provided with the described methods and compositions, such as nutraceutical formulations and dietary supplements, comprising C16:1n7-palmitoleate or one or more derivatives thereof exhibits a fasting baseline plasma, serum or red blood cell membrane C16:1n7-palmitoleate level not greater than about 150 µg/ml, not greater than about 100 µg/ml, not greater than about 50 µg/ml, not greater than about 25 µg/ml, not greater than about 10 µg/ml, or not greater than about 1 µg/ml.

In another embodiment, methods described herein comprise a step of measuring the subject's (or subject group's mean) baseline lipid profile prior to administering the compositions described herein. In another embodiment, methods comprise the step of identifying a subject or subject group having one or more of the following: baseline non-HDL-C value of about 200 mg/dl to about 400 mg/dl, for example at least about 210 mg/dl, at least about 220 mg/dl, at least about 230 mg/dl, at least about 240 mg/dl, at least about 250 mg/dl, at least about 260 mg/dl, at least about 270 mg/dl, at least about 280 mg/dl, at least about 290 mg/dl, or at least about 300 mg/dl; baseline total cholesterol value of about 250 mg/dl to about 400 mg/dl, for example at least about 260 mg/dl, at least about 270 mg/dl, at least about 280 mg/dl or at least about 290 mg/dl; baseline vLDL-C value of about 140 mg/dl to about 200 mg/dl, for example at least about 150 mg/dl, at least about 160 mg/dl, at least about 170 mg/dl, at least about 180 mg/dl or at least about 190 mg/dl; baseline HDL-C value of about 10 to about 60 mg/dl, for example not more than about 40 mg/dl, not more than about 35 mg/dl, not more than about 30 mg/dl, not more than about 25 mg/dl, not more than about 20 mg/dl, or not more than about 15 mg/dl; and/or baseline LDL-C value of about 50 to about 300 mg/dl, for example not less than about 100 mg/dl, not less than about 90 mg/dl, not less than about 80 mg/dl, not less than about 70 mg/dl, not less than about 60 mg/dl or not less than about 50 mg/dl.

In a related embodiment, compositions are provided, such as nutraceutical formulations and dietary supplements, comprising C16:1n7-palmitoleate or one or more derivatives thereof, are administered to a subject or a subject group for a period of about 1 to about 200 weeks, about 1 to about 100 weeks, about 1 to about 50 weeks, about 1 to about 20 weeks, about 1 to about 15 weeks, about 1 to about 10 weeks, about 1 to about 5 weeks, about 1 to about 2 weeks, or about 1 week, during which the subject or subject group exhibits one or more of the following outcomes:

(a) reduced triglyceride levels compared to baseline; (b) reduced Apo B levels compared to baseline; (c) increased HDL-C levels compared to baseline; (d) no increase in LDL-C levels compared to baseline; (e) a reduction in LDL-C levels compared to baseline; (f) a reduction in non-HDL-C levels compared to baseline; (g) a reduction in vLDL levels compared to baseline; (h) an increase in apo A-I levels compared to baseline; (i) an increase in apo A-I/apo B ratio compared to baseline; (j) a reduction in lipoprotein A levels compared to baseline; (k) a reduction in LDL particle number compared to baseline; (l) an increase in LDL size compared to baseline; (m) a reduction in remnant-like particle cholesterol compared to baseline; (n) a reduction in oxidized LDL compared to baseline; (o) no change or a reduction in fasting plasma glucose (FPG) compared to baseline; (p) a reduction in hemoglobin $A_{1c}$ ($HbA_{1c}$) compared to baseline; (q) a reduction in homeostasis model insulin resistance compared to baseline; (r) a reduction in lipoprotein associated phospholipase A2 compared to baseline; (s) a reduction in intracellular adhesion molecule-1 compared to baseline; (t) a reduction in interleukin-6 compared to baseline; (u) a reduction in plasminogen activator inhibitor-1 compared to baseline; (v) a reduction in high sensitivity C-reactive protein (hsCRP) compared to baseline; (w) an increase in serum or plasma C16:1n7-palmitoleate compared to baseline; (x) an increase in red blood cell (RBC) membrane C16:1n7-palmitoleate compared to baseline; and/or (y) a reduction or increase in one or more of serum phospholipid and/or red blood cell content of palmitic acid (PA), staeridonic acid (SA) or oleic acid (OA) compared to baseline.

In one embodiment, upon administering or providing compositions, such as nutraceutical formulations and dietary supplements, comprising C16:1n7-palmitoleate or one or more derivatives thereof to a subject, the subject exhibits a decrease in triglyceride levels, an increase in the concentrations of C16:1n7-palmitoleate in red blood cells, and an increase of the ratio of C16:1n7-palmitoleate relative to palmitic acid (C16:1n7-palmitoleate:palmitic acid) in red blood cells.

In one embodiment, methods are provided that comprise measuring baseline levels of one or more markers set forth in (a)-(y) above prior to dosing the subject or subject group. In another embodiment, the methods comprise administering a composition as disclosed herein to the subject after baseline levels of one or more markers set forth in (a)-(y) are determined, and subsequently taking an additional measurement of said one or more markers.

In another embodiment, upon treatment with compositions, such as nutraceutical formulations and dietary supplements, comprising C16:1n7-palmitoleate or one or more derivatives thereof, for example over a period of about 1 to about 200 weeks, about 1 to about 100 weeks, about 1 to about 50 weeks, about 1 to about 20 weeks, about 1 to about 10 weeks, about 1 to about 5 weeks, about 1 to about 2 weeks, or about 1 week, the subject or subject group exhibits any 2 or more of, any 3 or more of, any 4 or more of, any 5 or more of, any 6 or more of, any 7 or more of, any 8 or more of, any 9 or more of, any 10 or more of, any 11 or more of, any 12 or more of, any 13 or more of, any 14 or more of, any 15 or more of, any 16 or more of, any 17 or more of, any 18 or more of, any 19 or more of, any 20 or more of, any 21 or more of, any 22 or more of, any 23 or more, any 24 or more, or all 25 of outcomes (a)-(y) described immediately above.

In another embodiment, upon treatment with a methods and compositions, such as nutraceutical formulations and dietary supplements, comprising C16:1n7-palmitoleate or one or more derivatives thereof, the subject or subject group exhibits one or more of the following outcomes:

(a) a reduction in triglyceride level of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) as compared to baseline;

(b) a less than 30% increase, less than 20% increase, less than 10% increase, less than 5% increase or no increase in non-HDL-C levels or a reduction in non-HDL-C levels of at least about 1%, at least about 3%, at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) as compared to baseline;

(c) substantially no change in HDL-C levels, no change in HDL-C levels, or an increase in HDL-C levels of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) as compared to baseline;

(d) a less than 60% increase, a less than 50% increase, a less than 40% increase, a less than 30% increase, less than 20% increase, less than 10% increase, less than 5% increase or no increase in LDL-C levels or a reduction in LDL-C levels of at least about 5%, at least about 10%, at least about 15%, at least about 20%, at least about 25%, at least about 30%, at least about 35%, at least about 40%, at least about 45%, at least about 50%, at least about 55%, at least about 55% or at least about 75% (actual % change or median % change) as compared to baseline;

(e) a decrease in Apo B levels of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) as compared to baseline;

(f) a reduction in vLDL levels of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(g) an increase in apo A-I levels of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(h) an increase in apo A-I/apo B ratio of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(i) a reduction in lipoprotein (a) levels of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(j) a reduction in mean LDL particle number of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(k) an increase in mean LDL particle size of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(l) a reduction in remnant-like particle cholesterol of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(m) a reduction in oxidized LDL of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(n) substantially no change, no significant change, or a reduction (e.g. in the case of a diabetic subject) in fasting plasma glucose (FPG) of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(o) substantially no change, no significant change or a reduction in hemoglobin $A_{1c}$ ($HbA_{1c}$) of at least about 5%, at least about 10%, at least about 15%, at least about 20%, at least about 25%, at least about 30%, at least about 35%, at least about 40%, at least about 45%, or at least about 50% (actual % change or median % change) compared to baseline;

(p) a reduction in homeostasis model index insulin resistance of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(q) a reduction in lipoprotein associated phospholipase A2 of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(r) a reduction in intracellular adhesion molecule-1 of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(s) a reduction in interleukin-6 of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(t) a reduction in plasminogen activator inhibitor-1 of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(u) a reduction in high sensitivity C-reactive protein (hsCRP) of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline;

(v) an increase in serum, plasma and/or RBC EPA of at least about 5%, at least about 10%, at least about 15%, at least about 20%, at least about 25%, at least about 30%, at least about 35%, at least about 40%, at least about 45%, at least about 50%, at least about 100%, at least about 200% or at least about 400% (actual % change or median % change) compared to baseline;

(w) an increase in serum phospholipid and/or red blood cell membrane EPA of at least about 5%, at least about 10%, at least about 15%, at least about 20%, at least about 25%, at least about 30%, at least about 35%, at least about 40%, at least about 45%, r at least about 50%, at least about 100%, at least about 200%, or at least about 400% (actual % change or median % change) compared to baseline;

(x) a reduction or increase in one or more of serum phospholipid and/or red blood cell DHA, DPA, AA, PA and/or OA of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) compared to baseline; and/or (y) a reduction in total cholesterol of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) compared to baseline.

In one embodiment, the methods comprise measuring baseline levels of one or more markers set forth in (a)-(y) prior to dosing the subject or subject group. In another embodiment, the methods comprise administering a composition as disclosed herein to the subject after baseline levels of one or more markers set forth in (a)-(y) are determined, and subsequently taking a second measurement of the one or more markers as measured at baseline for comparison thereto.

In another embodiment, upon treatment with a composition described herein, for example over a period of about 1 to about 200 weeks, about 1 to about 100 weeks, about 1 to about 80 weeks, about 1 to about 50 weeks, about 1 to about 40 weeks, about 1 to about 20 weeks, about 1 to about 15 weeks, about 1 to about 12 weeks, about 1 to about 10 weeks, about 1 to about 5 weeks, about 1 to about 2 weeks or about 1 week, the subject or subject group exhibits any 2 or more of, any 3 or more of, any 4 or more of, any 5 or more of, any 6 or more of, any 7 or more of, any 8 or more of, any 9 or more of, any 10 or more of, any 11 or more of, any 12 or more of, any 13 or more of, any 14 or more of, any 15 or more of, any 16 or more of, any 17 or more of, any 18 or more of, any 19 or more of, any 20 or more of, any 21 or more of, any 22 or more of, any 23 or more of, any 24 or more of, or all 26 or more of outcomes (a)-(y) described immediately above.

Parameters (a)-(y) can be measured in accordance with any clinically acceptable methodology. For example, triglycerides, total cholesterol, HDL-C and fasting blood sugar can be sample from serum and analyzed using standard photometry techniques. VLDL-TG, LDL-C and VLDL-C can be calculated or determined using serum lipoprotein fractionation by preparative ultracentrifugation and subsequent quantitative analysis by refractometry or by analytic ultracentrifugal methodology. Apo A1, Apo B and hsCRP can be determined from serum using standard nephelometry techniques. Lipoprotein (a) can be determined from serum using standard turbidimetric immunoassay techniques. LDL particle number and particle size can be determined using nuclear magnetic resonance (NMR) spectrometry. Remnants lipoproteins and LDL-phospholipase A2 can be determined from EDTA plasma or serum and serum, respectively, using enzymatic immunoseparation techniques. Oxidized LDL, intercellular adhesion molecule-1 and interleukin-6 levels can be determined from serum using standard enzyme immunoassay techniques. These techniques are described in detail in standard textbooks, for example Tietz Fundamentals of Clinical Chemistry, $6^{th}$ Ed. (Burtis, Ashwood and Borter Eds.), WB Saunders Company.

In one embodiment, subjects fast for up to 12 hours prior to blood sample collection, for example about 10 hours.

In another embodiment, methods and compositions are provided, such as nutraceutical formulations and dietary supplements, comprising C16:1n7-palmitoleate or one or more derivatives thereof for treating or preventing primary hypercholesterolemia and/or mixed dyslipidemia (Fredrickson Types IIa and IIb) in a patient in need thereof, comprising administering to the patient one or more compositions as disclosed herein. In a related embodiment, a method is provided of reducing triglyceride levels in a subject or subjects when treatment with a statin or niacin extended-release monotherapy is considered inadequate (Frederickson type IV hyperlipidemia).

In another embodiment, methods and compositions are provided, such as nutraceutical formulations and dietary supplements, comprising C16:1n7-palmitoleate or one or more derivatives thereof for treating or preventing risk of recurrent nonfatal myocardial infarction in a patient with a history of myocardial infarction, comprising administering to the patient one or more compositions as disclosed herein.

In another embodiment, methods and compositions are provided, such as nutraceutical formulations and dietary supplements, comprising C16:1n7-palmitoleate or one or more derivatives thereof for slowing progression of or promoting regression of atherosclerotic disease in a patient in need thereof, comprising administering to a subject in need thereof one or more compositions as disclosed herein.

In another embodiment, methods and compositions are provided, such as nutraceutical formulations and dietary supplements, comprising C16:1n7-palmitoleate or one or more derivatives thereof for treating or preventing very high serum triglyceride levels (e.g. Types IV and V hyperlipidemia) in a patient in need thereof, comprising administering to the patient one or more compositions as disclosed herein.

In another embodiment, methods and compositions are provided, such as nutraceutical formulations and dietary supplements, comprising C16:1n7-palmitoleate or one or more derivatives thereof for treating subjects having very high serum triglyceride levels (e.g., greater than 1000 mg/dl or greater than 2000 mg/dl) and that are at risk of developing pancreatitis, comprising administering to the patient one or more compositions as disclosed herein.

In further aspects, methods and compositions are provided, such as nutraceutical formulations and dietary supplements, comprising C16:1n7-palmitoleate or one or more derivatives thereof for increasing the ratio of high-density lipoprotein (HDL) relative to low-density lipoprotein (LDL) in the blood serum of a subject. The methods typically involve an oral administration of a composition, such as a dietary supplement, comprising C16:1n7-palmitoleate or one or more derivatives thereof. In certain embodiments, methods and compositions are provided, such as nutraceutical formulations and dietary supplements, comprising C16:1n7-palmitoleate or one or more derivatives thereof are useful for increasing the ratio of apolipoprotein A1 (Apo-A1) relative to apolipoprotein B (Apo-B) in the blood serum of a subject.

In certain aspects, the dietary supplement is administered to a subject in combination with a lipid-lowering or cholesterol-lowering agent. In some embodiments, the cholesterol-lowering agent is an HMG-CoA reductase inhibitor (e.g., a statin, such as rosuvastatin (Crestor®), lovastatin (Mevacor®), cerivastatin (Baycol®), fluvastatin (Lescol®), simvastatin (Zocor®), pravastatin (Pravachol®) and atorvastatin (Lipitor®)), a fibrate (e.g., clofibrate (Atromid-S®)), a bile acid sequestrant (e.g., cholestyramine and colestipol (Colestid®), and nicotinic acid (niacin)), gemfibrozil (Lopid® and Gemcor®), ezetimibe therapy, and probucol (Panavir®). In some embodiments, a statin is utilized selected from the following group: atorvastatin, rosuvastatin, fluvastatin, lovastatin, pravastatin, and simvastatin.

Pravastatin, which is known in the market as Pravachol® manufactured by Bristol-Myers Squibb, Princeton, N.J., is hydrophilic. Pravastatin is best absorbed without food, i.e., on an empty stomach. The dosage of pravastatin in the combined administration of C16:1n7-palmitoleate or one or more derivatives thereof is from 2.5 to 80 mg, 5 to 60 mg, or from 10 to 40 mg per dosage of C16:1n7-palmitoleate or one or more derivatives thereof. In one variation, the combination product using pravastatin is taken at or around bedtime, e.g., 10 pm.

Lovastatin, which is marketed under the name Mevacor® by Merck, Whitehouse Station, N.J., is hydrophobic. Unlike pravastatin, lovastatin should be taken with meals and accordingly, in some embodiments, the combination product of C16:1n7-palmitoleate or one or more derivatives thereof and lovastatin should be taken with food. The dosage of lovastatin, in the combined administration of C16:1n7-palmitoleate or one or more derivatives thereof is from 2.5 to 100 mg, 5 to 80 mg, or from 10 to 40 mg per dosage of C16:1n7-palmitoleate or one or more derivatives thereof.

Simvastatin, which is marketed under the name Zocor® by Merck, Whitehouse Station, N.J., is hydrophobic. The dosage of simvastatin, in the combined administration of C16:1n7-palmitoleate or one or more derivatives thereof is from 1 to 80 mg per day, 2 to 60 mg, or from 5 to 40 mg per dosage of C16:1n7-palmitoleate or one or more derivatives thereof.

Atorvastatin, which is marketed under the name Lipitor® by Pfizer, New York, N.Y., is hydrophobic and is known as a synthetic statin. The dosage of atorvastatin, in the combined administration of C16:1n7-palmitoleate or one or more derivatives thereof is from 2.5 to 100 mg, 5 to 80 mg, or from 10 to 40 mg per dosage of C16:1n7-palmitoleate or one or more derivatives thereof.

Fluvastatin, which is marketed under the name Lescol® by Novartis, New York, N.Y., is hydrophilic and is known as a synthetic statin. The dosage of fluvastatin, in the combined administration of C16:1n7-palmitoleate or one or more derivatives thereof is from 5 to 160 mg, 10 to 120 mg, or from 20 to 80 mg per dosage of C16:1n7-palmitoleate or one or more derivatives thereof.

Rosuvastatin is marketed under the name Crestor® by Astra Zeneca, Wilmington, Del. The dosage of rosuvastatin, in the combined administration of C16:1n7-palmitoleate or one or more derivatives thereof is from 1 to 80 mg, 2 to 60 mg, or from 5 to 40 mg per dosage of C16:1n7-palmitoleate or one or more derivatives thereof.

The lipid-lowering or cholesterol-lowering agent may be administered in an amount more than, equal to or less than the conventional full-strength dose as a single-administered product. For example, the lipid-lowering or cholesterol-lowering agent may be administered in an amount of from 10-100%, about 25-100%, or about 50-80%, of the conventional full-strength dose as a single-administered product. In one embodiment, a statin, for example, can generally be present in an amount from about 0.5 mg to 80 mg, from about 1 mg to about 40 mg, or from about 5 mg to about 20 mg, per gram of C16:1n7-palmitoleate or one or more derivatives thereof. The daily dose may range from about 2 mg to about 320 mg, or about 4 mg to about 160 mg.

The daily dosages of the lipid-lowering or cholesterol-lowering agent and C16:1n7-palmitoleate or one or more derivatives thereof can be administered together in from 1 to 10 dosages, from 1 to 4 times a day, or from 1 to 2 times a day. The administration may be an oral administration, although other forms of administration that provides a unit dosage of lipid-lowering or cholesterol-lowering agent and C16:1n7-palmitoleate or one or more derivatives thereof may be used.

In some embodiments, the formulations allow for improved effectiveness of each active ingredient, with one or both administered as a conventional full-strength dose, as compared to the formulations in the prior art. In other embodiments, the formulations may allow for reduced dosages of lipid-lowering or cholesterol-lowering agent and/or C16:1n7-palmitoleate or one or more derivatives thereof, as compared to the formulations in the prior art, while still maintaining or even improving upon the effectiveness of each active ingredient.

The present combination of a lipid-lowering or cholesterol-lowering agent and C16:1n7-palmitoleate or one or more derivatives thereof may allow for a greater effect than any expected combined or additive effect of the two drugs alone. Moreover, the combined or additive effect of the two drugs may depend on the initial level of triglycerides in the blood of a subject. For example, the triglyceride level of a subject is generally as normal if less than 150 mg/dL, borderline to high if within about 150-199 mg/dL, high if within about 200-499 mg/dL and very high if 500 mg/dL or higher. The present methods and compositions may be used to reduce the triglyceride level of a "very high" down to a "high" or "borderline to high" in less than 48 weeks, optionally within 24 weeks, or within 12 weeks, or within 6 weeks, 4 weeks, or 2 weeks. The present methods and compositions may also be used to reduce the triglyceride level of a "high" down to a "borderline to high" or "normal" in less than 48 weeks, or within 24 weeks, or within 12 weeks, or within 6 weeks, 4 weeks, or 2 weeks.

Thus, the combined treatment of the two active ingredients, separately or through the novel combination product of the present compositions, may cause an unexpected increase in effect of the active ingredients that allows increased effectiveness with standard dosages or maintained effectiveness with reduced dosages of the two active ingredients. It is well accepted in practice that an improved bioavailability or effectiveness of a drug or other active ingredient allows for an appropriate reduction in the daily dosage amount. Any undesirable side effects may also be reduced as a result of the lower dosage amount and the reduction in excipients (e.g., surfactants).

The utilization of a single administration of a combination of a lipid-lowering or cholesterol-lowering agent and C16:1n7-palmitoleate or one or more derivatives thereof overcomes the limitations of the prior art by improving the efficacy of the lipid-lowering or cholesterol-lowering agent and C16:1n7-palmitoleate or one or more derivatives thereof, and allows for a treatment with improved effectiveness and less excipients than in multiple administrations of lipid-lowering or cholesterol-lowering agent and C16:1n7-palmitoleate or one or more derivatives thereof.

The administration of a combination of lipid-lowering or cholesterol-lowering agent and C16:1n7-palmitoleate or one or more derivatives thereof achieves results that are highly advantageous and beneficial. The increased efficacy of the combined treatment and combination product allows for a novel and more efficient pharmaceutical and nutraceutical treatment for coronary artery disease, the accumulation of cholesterol or lipid deposits in the blood vessels of a subject, hypertriglyceridemia, hypercholesterolemia, mixed dyslipidemia, vascular disease, atherosclerotic disease and related conditions.

C16:1n7-Palmitoleate

The compositions comprising C16:1n7-palmitoleate or one or more derivatives thereof have demonstrated surprising efficacy in treating clinical manifestations of cardiovascular disease. The compositions comprise active C16:1n7-palmitoleate or one or more derivatives thereof, nutraceutical formulations thereof, dietary supplements thereof, and pharmaceutical formulations thereof.

Nutraceutical formulations or dietary supplements, comprising C16:1n7-palmitoleate or its derivatives are provided herein for the prevention or mitigation of cardiovascular disease, related disease states such as coronary artery disease and the accumulation of cholesterol or lipid deposits in the blood vessels of a subject. One non-limiting advantage of the dietary supplements or neutraceutical compositions is that they are very well tolerated, not giving rise to any appreciable side effects.

The dietary supplements and neutraceutical compositions comprise C16:1n7-palmitoleate or one or more derivatives thereof. In certain embodiments, the C16:1n7-palmitoleate derivative is C16:1n7-palmitoleic acid. In further embodiments, the C16:1n7-palmitoleate derivative is cis-C16:1n7-palmitoleic acid. In some embodiments, the C16:1n7-palmitoleate derivative is a metal salt (e.g., Na$^+$, K$^+$, or Li$^+$) of cis-C16:1n7-palmitoleate. In further embodiments, the C16:1n7-palmitoleate derivative is an ester (e.g., $(C_1-C_4)$alkyl ester, methyl, ethyl, propyl, monoglyceride, diglyceride, triglyceride, or a combination thereof.) of cis-C16:1n7-palmitoleate. In further embodiments, the C16:1n7-palmitoleate derivative is a methyl ester, ethyl ester, propyl ester of cis-C16:1n7-palmitoleate. In one embodiment, the cis-C16:1n7-palmitoleate ester is the ethyl ester.

In further embodiments, the C16:1n7-palmitoleate derivative is trans-C16:1n7-palmitoleic acid. In some embodiments, the C16:1n7-palmitoleate derivative is a metal salt (e.g., Na$^+$, K$^+$, or Li$^+$) of trans-C16:1n7-palmitoleate. In further embodiments, the C16:1n7-palmitoleate derivative is an ester (e.g., methyl, ethyl, propyl, mono-, di-, or triglyceride) of trans-C16:1n7-palmitoleate.

In certain embodiments, the C16:1n7-palmitoleate derivative is of the formula I or II:

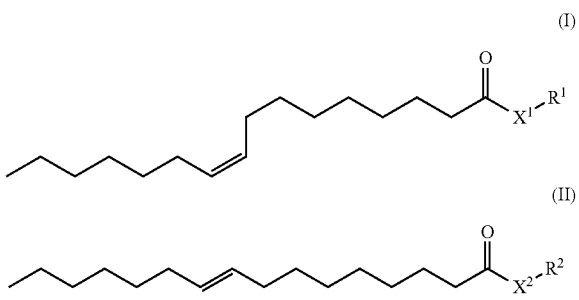

wherein
each $X^1$ and $X^2$ is, independently, O, S, NH, NR$_A$, or N(C$_1$-C$_4$)alkyl;
each $R^1$ and $R^2$ is, independently, a metal cation, hydrogen, R$_B$, (C$_1$-C$_4$)alkyl, a monoglyceride, diglyceride, or triglyceride; and
each R$_A$ and R$_B$ is, independently, a hydrogen, an aliphatic moiety, a heteroaliphatic moiety, an acyl moiety; an aryl moiety; or a heteroaryl moiety.

In some embodiments, the C16:1n7-palmitoleate derivative is a cis-palmitoleate derivative of formula (I). In some embodiments, the C16:1n7-palmitoleate derivative is a trans-palmitoleate derivative of formula (II).

In some embodiments, $X^1$ is O. In other embodiments, $X^1$ is S. In other embodiments, $X^1$ is NH. In other embodiments, $X^1$ is NR$_A$. In other embodiments, $X^1$ is N—(C$_1$-C$_4$)alkyl. In some embodiments, $X^1$ is N-n-butyl. In other embodiments, $X^1$ is N-sec-butyl. In some embodiments, $X^1$ is N-iso-butyl. In other embodiments, $X^1$ is N-tert-butyl. In other embodiments, $X^1$ is N-n-propyl. In some embodiments, $X^1$ is N-iso-propyl. In other embodiments, $X^1$ is N-ethyl. In some embodiments, $X^1$ is N-methyl. In some embodiments, $X^2$ is O. In other embodiments, $X^2$ is S. In other embodiments, $X^2$ is NH. In other embodiments, $X^2$ is NR$_A$. In other embodiments, $X^2$ is N—(C$_1$-C$_4$)alkyl. In other embodiments, $X^2$ is N—(C$_1$-C$_3$)alkyl. In some embodiments, $X^2$ is N-n-butyl. In other embodiments, $X^2$ is N-sec-butyl. In some embodiments, $X^2$ is N-iso-butyl. In other embodiments, $X^2$ is N-tert-butyl. In other embodiments, $X^2$ is N-n-propyl. In some embodiments, $X^2$ is N-iso-propyl. In other embodiments, $X^2$ is N-ethyl. In some embodiments, $X^2$ is N-methyl.

In some embodiments, $R^1$ is a metal cation. In some embodiments, $R^1$ is Na$^+$. In some embodiments, $R^1$ is K$^+$. In some embodiments, $R^1$ is Li$^+$. In some embodiments, $R^1$ is hydrogen. In other embodiments, $R^1$ is R$_B$. In other embodiments, $R^1$ is (C$_1$-C$_4$)alkyl. In other embodiments, $R^1$ is (C$_1$-C$_3$)alkyl. In some embodiments, $R^1$ is n-butyl. In other embodiments, $R^1$ is sec-butyl. In some embodiments, $R^1$ is iso-butyl. In other embodiments, $R^1$ is tert-butyl. In other embodiments, $R^1$ is n-propyl. In some embodiments, $R^1$ is iso-propyl. In other embodiments, $R^1$ is ethyl. In some embodiments, $R^1$ is methyl. $R^2$ is a metal cation. In some embodiments, $R^2$ is Na$^+$. In some embodiments, $R^2$ is K$^+$. In some embodiments, $R^2$ is Li$^+$. In some embodiments, $R^2$ is hydrogen. In other embodiments, $R^2$ is $R_B$. In other embodiments, $R^2$ is $(C_1\text{-}C_4)$alkyl. In other embodiments, $R^2$ is $(C_1\text{-}C_3)$alkyl. In some embodiments, $R^2$ is n-butyl. In other embodiments, $R^2$ is sec-butyl. In some embodiments, $R^2$ is iso-butyl. In other embodiments, $R^2$ is tert-butyl. In other embodiments, $R^2$ is n-propyl. In some embodiments, $R^2$ is iso-propyl. In other embodiments, $R^2$ is ethyl. In some embodiments, $R^2$ is methyl.

In certain embodiments of the C16:1n7-palmitoleate derivative of formula (I) or (II), each $X^1$ and $X^2$ is O and each $R^1$ and $R^2$ is hydrogen. In other embodiments of the C16:1n7-palmitoleate derivative of formula (I) or (II), each $X^1$ and $X^2$ is O and each $R^1$ and $R^2$ is a metal cation. In other embodiments of the C16:1n7-palmitoleate derivative of formula (I) or (II), each $X^1$ and $X^2$ is O and each $R^1$ and $R^2$ is $R_B$. In other embodiments of the C16:1n7-palmitoleate derivative of formula (I) or (II), each $X^1$ and $X^2$ is O and each $R^1$ and $R^2$ is $(C_1\text{-}C_4)$alkyl. In other embodiments of the C16:1n7-palmitoleate derivative of formula (I) or (II), each $X^1$ and $X^2$ is O and each $R^1$ and $R^2$ is methyl. In other embodiments of the C16:1n7-palmitoleate derivative of formula (I) or (II), each $X^1$ and $X^2$ is O and each $R^1$ and $R^2$ is ethyl.

In certain embodiments, each $X^1$ and $X^2$ is O and the C16:1n7-palmitoleate derivative of formula (I) or (II) is the monoglyceride. In certain embodiments, each $X^1$ and $X^2$ is O and the C16:1n7-palmitoleate derivative of formula (I) or (II) is the diglyceride. In certain embodiments, each $X^1$ and $X^2$ is O and the C16:1n7-palmitoleate derivative of formula (I) or (II) is the triglyceride.

In certain embodiments, each $X^1$ and $X^2$ is O and the C16:1n7-palmitoleate derivative of formula (I) is the methyl ester. In certain embodiments, each $X^1$ and $X^2$ is O and the C16:1n7-palmitoleate derivative of formula (I) is the ethyl ester.

In certain embodiments of the C16:1n7-palmitoleate derivative of formula (I) or (II), each $X^1$ and $X^2$ is S and each $R^1$ and $R^2$ is hydrogen. In other embodiments of the C16:1n7-palmitoleate derivative of formula (I) or (II), each $X^1$ and $X^2$ is S and each $R^1$ and $R^2$ is a metal cation. In other embodiments of the C16:1n7-palmitoleate derivative of formula (I) or (II), each $X^1$ and $X^2$ is S and each $R^1$ and $R^2$ is $R_B$. In other embodiments of the C16:1n7-palmitoleate derivative of formula (I) or (II), each $X^1$ and $X^2$ is S and each $R^1$ and $R^2$ is $(C_1\text{-}C_4)$alkyl. In other embodiments of the C16:1n7-palmitoleate derivative of formula (I) or (II), each $X^1$ and $X^2$ is S and each $R^1$ and $R^2$ is methyl. In other embodiments of the C16:1n7-palmitoleate derivative of formula (I) or (II), each $X^1$ and $X^2$ is S and each $R^1$ and $R^2$ is ethyl.

In certain embodiments of the C16:1n7-palmitoleate derivative of formula (I) or (II), each $X^1$ and $X^2$ is NH and each $R^1$ and $R^2$ is hydrogen. In other embodiments of the C16:1n7-palmitoleate derivative of formula (I) or (II), each $X^1$ and $X^2$ is NH and each $R^1$ and $R^2$ is $R_B$. In other embodiments of the C16:1n7-palmitoleate derivative of formula (I) or (II), each $X^1$ and $X^2$ is NH and each $R^1$ and $R^2$ is $(C_1\text{-}C_4)$alkyl. In other embodiments of the C16:1n7-palmitoleate derivative of formula (I) or (II), each $X^1$ and $X^2$ is NH and each $R^1$ and $R^2$ is methyl. In other embodiments of the C16:1n7-palmitoleate derivative of formula (I) or (II), each $X^1$ and $X^2$ is NH and each $R^1$ and $R^2$ is ethyl. In other embodiments of the C16:1n7-palmitoleate derivative of formula (I) or (II), each $X^1$ and $X^2$ is $N(C_1\text{-}C_4)$alkyl and each $R^1$ and $R^2$ is $R_B$. In other embodiments of the C16:1n7-palmitoleate derivative of formula (I) or (II), each $X^1$ and $X^2$ is $N(C_1\text{-}C_4)$alkyl and each $R^1$ and $R^2$ is $(C_1\text{-}C_4)$alkyl. In other embodiments of the C16:1n7-palmitoleate derivative of formula (I) or (II), each $X^1$ and $X^2$ is N-methyl and each $R^1$ and $R^2$ is methyl. In other embodiments of the C16:1n7-palmitoleate derivative of formula (I) or (II), each $X^1$ and $X^2$ is N-ethyl and each $R^1$ and $R^2$ is ethyl.

The term "aliphatic", as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups contain 1-20 aliphatic carbon atoms. In certain other embodiments, the alkyl, alkenyl, and alkynyl groups contain 1-10 aliphatic carbon atoms. In yet other embodiments, the alkyl, alkenyl, and alkynyl groups contain 1-8 aliphatic carbon atoms. In still other embodiments, the alkyl, alkenyl, and alkynyl groups contain 1-6 aliphatic carbon atoms. In yet other embodiments, the alkyl, alkenyl, and alkynyl groups contain 1-4 carbon atoms. Illustrative aliphatic groups thus include, but are not limited to, for example, methyl, ethyl, n-propyl, isopropyl, cyclopropyl, —CH$_2$-cyclopropyl, vinyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl(propargyl), 1-propynyl, and the like.

The term "heteroaliphatic" as used herein, refers to aliphatic moieties that contain one or more oxygen, sulfur, nitrogen, phosphorus, or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_C$; —CO$_2$(R$_C$); —CON(R$_C$)$_2$; —OC(O)R$_C$; —OCO$_2$R$_C$; —OCON(R$_C$)$_2$; —N(R$_C$)$_2$; —S(O)$_2$R$_C$; —NR$_C$(CO)R$_C$, wherein each occurrence of R$_C$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted.

In general, the terms "aryl" and "heteroaryl", as used herein, refer to stable mono- or polycyclic, heterocyclic, polycyclic, and polyheterocyclic unsaturated moieties having 3-14 carbon atoms, each of which may be substituted or unsubstituted. Substituents include, but are not limited to, any of the previously mentioned substitutents, i.e., the substituents recited for aliphatic moieties, or for other moieties as disclosed herein, resulting in the formation of a stable compound. In certain embodiments, "aryl" refers to a mono- or bicyclic carbocyclic ring system having one or two aromatic rings including, but not limited to, phenyl, naphthyl, tetrahydronaphthyl, indanyl, indenyl, and the like. In certain embodiments, the term "heteroaryl", as used herein, refers to a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups can be unsubstituted or substituted, wherein substitution includes replacement of one, two, three, or more of the hydrogen atoms thereon independently with any one or more of the following moieties including, but not limited to: aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_D$; —CO$_2$(R$_D$); —CON(R$_D$)$_2$; —OC(O)R$_D$; —OCO$_2$R$_D$; —OCON(R$_D$)$_2$; —N(R$_D$)$_2$; —S(O)$_2$R$_D$; —NR$_D$(CO)R$_D$, wherein each occurrence of R$_D$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted.

The term "acyl," as used herein, refers to a group having the general formula —C(=O)R$_E$, —C(=O)OR$_E$, —C(=O)—O—C(=O)R$_E$, —C(=O)SR$_E$, —C(=O)N(R$_E$)$_2$, —C(=S)R$_E$, —C(=S)N(R$_E$)$_2$, and —C(=S)S(R$_E$), —C(=NR$_E$)R$_E$, —C(=NR$_E$)OR$_E$, —C(=NR$_E$)SR$_E$, and —C(=NR$_E$)N(R$_E$)$_2$, wherein R$_E$ is hydrogen; halogen; optionally substituted hydroxyl; optionally substituted thiol; optionally substituted amino; cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; optionally substituted aryl, optionally substituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$_E$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, and the like, each of which may or may not be further substituted).

The general principles of organic chemistry can be routinely used by those of ordinary skill in the art to prepare the compounds of the compositions described herein. Such principles are described, for example, in *Organic Chemistry*, Thomas Sorrell, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987.

As indicated, the compositions, such as a neutraceutical or a dietary supplement, comprise C16:1n7-palmitoleate or derivatives thereof. In some aspects, the composition comprises a C16:1n7-palmitoleate derivative, wherein the wt % of the C16:1n7-palmitoleate derivative exceeds the wt % of any other single ingredient in the composition. In certain embodiments, the composition, such as a neutraceutical or a dietary supplement, comprises between 1% to 100% of C16:1n7-palmitoleate and its derivatives relative to all of the components of the neutraceutical composition. In some embodiments, the composition comprises from about 5% to about 20%, from about 20% to about 30%, or at least about 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of C16:1n7-palmitoleate or one or more derivatives thereof relative to all of the components of the neutraceutical composition.

In some embodiments, the composition, such as a neutraceutical or a dietary supplement, comprises from about 30 wt % to about 90 wt % of the C16:1n7-palmitoleate derivative. In other embodiments, the composition comprises from about 35 wt % to about 70 wt % of the C16:1n7-palmitoleate derivative. In some embodiments, the composition comprises from about 30% to about 60 wt % of the C16:1n7-palmitoleate derivative. In other embodiments, the composition comprises about 45% of the C16:1n7-palmitoleate derivative. In other embodiments, the dietary supplement comprises about 30% of the C16:1n7-palmitoleate derivative. In other embodiments, the dietary supplement comprises about 40% of the C16:1n7-palmitoleate derivative. In other embodiments, the dietary supplement comprises about 50% of the C16:1n7-palmitoleate derivative. In other embodiments, the dietary supplement comprises about 60% of the C16:1n7-palmitoleate derivative. In other embodiments, the dietary supplement comprises about 70% of the C16:1n7-palmitoleate derivative. In other embodiments, the dietary supplement comprises about 80% of the C16:1n7-palmitoleate derivative. In each of the above embodiments, the composition further comprises additional fatty acids that extend the shelf-life of the composition.

In certain embodiments, the composition, such as a neutraceutical or a dietary supplement, comprises between 1% to 100% of C16:1n7-palmitoleate and its derivatives relative to all of the fatty acids and fatty acid derivatives that are present in the composition. In some embodiments, the composition comprises from about 5% to about 20%, from about 20% to about 30%, or at least about 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of C16:1n7-palmitoleate or one or more derivatives thereof relative to all of the fatty acids and fatty acid derivatives that are present in the composition.

In certain embodiments, the composition, such as a neutraceutical or a dietary supplement, comprises C16:1n7-palmitoleate and its derivatives and further comprises C14:1n5-myristoleate and its derivatives. The composition may comprise either more, less, or substantially the same amount of C16:1n7-palmitoleate and its derivatives relative to C14:1n5-myristoleate and its derivatives. Typically, the composition comprises C16:1n7-palmitoleate and its derivatives relative to C14:1n5-myristoleate and its derivatives in a ratio in excess of 1:1. In certain embodiments, the composition comprises a ratio of C16:1n7-palmitoleate and its derivatives relative to C14:1n5-myristoleate and its derivatives (i.e., palmitoleate:C14:1n5-myristoleate), wherein the ratio is in excess of 1.1:1, 1.2:1, 1.3:1, 1.4:1, 1.5:1, 1.6:1, 1.7:1, 1.8:1, 1.9:1, 2.0:1, 2.1:1, 2.2:1, 2.3:1, 2.4:1, 2.5:1, 2.6:1, 2.7:1, 2.8:1, 2.9:1, 3.0:1, 3.1:1, 3.2:1, 3.3:1, 3.4:1, 3.5:1, 3.6:1, 3.7:1, 3.8:1, 3.9:1, 4.0:1, 4.1:1, 4.2:1, 4.3:1, 4.4:1, 4.5:1, 4.6:1, 4.7:1, 4.8:1, 4.9:1, 5.0:1, 5.1:1, 5.2:1, 5.3:1, 5.4:1, 5.5:1, 5.6:1, 5.7:1, 5.8:1, 5.9:1, 6.0:1, 6.1:1, 6.2:1, 6.3:1, 6.4:1, 6.5:1, 6.6:1, 6.7:1, 6.8:1, 6.9:1, 7.0:1, 7.1:1, 7.2:1, 7.3:1, 7.4:1, 7.5:1, 7.6:1, 7.7:1, 7.8:1, 7.9:1, 8.0:1, 8.1:1, 8.2:1, 8.3:1, 8.4:1, 8.5:1, 8.6:1, 8.7:1, 8.8:1, 8.9:1, 9.0:1, 9.1:1, 9.2:1, 9.3:1, 9.4:1, 9.5:1, 9.6:1, 9.7:1, 9.8:1, 9.9:1, 10.0:1, 11:1, 12:1, 13:1, 14:1, 15:1, 16:1, 17:1, 18:1, 19:1, 20:1, 25:1, 30:1, 35:1, 40:1, 45:1, 50:1, 55:1, 60:1, 65:1, 70:1, 75:1, 80:1, 85:1, 90:1, 95:1, or 100:1.

In some embodiments, the composition, such as a neutraceutical or a dietary supplement, further comprises a palmitate derivative, wherein the ratio of the C16:1n7-palmitoleate derivative to the palmitate derivative (i.e., palmitoleate:palmitate) is from about 2:1 to about 50:1. In other embodiments, the ratio of the C16:1n7-palmitoleate derivative to the palmitate derivative (i.e., palmitoleate:palmitate) is from about 5:1 to about 10:1. In some embodiments, the ratio of the C16:1n7-palmitoleate derivative to the palmitate derivative (i.e., palmitoleate:palmitate) is from about 10:1 to about 20:1. In some embodiments, the ratio of the C16:1n7-palmitoleate derivative to the palmitate derivative (i.e., palmitoleate:palmitate) is from about 20:1 to about 50:1.

In certain embodiments, the composition, such as a neutraceutical or a dietary supplement, comprises C16:1n7-palmitoleate and its derivatives and further comprises C16:0-palmitate and its derivatives. The composition may comprise either more, less, or substantially the same amount of C16:1n7-palmitoleate and its derivatives relative to C16:0-palmitate and its derivatives. Typically, the composition comprises C16:1n7-palmitoleate and its derivatives relative to C16:0-palmitate and its derivatives in a ratio in excess of 1:1. In certain embodiments, the composition comprises a ratio of C16:1n7-palmitoleate and its derivatives relative to C16:0-palmitate and its derivatives (i.e., palmitoleate:palmitate), wherein the ratio is in excess of 1.1:1, 1.2:1, 1.3:1, 1.4:1, 1.5:1, 1.6:1, 1.7:1, 1.8:1, 1.9:1, 2.0:1, 2.1:1, 2.2:1, 2.3:1, 2.4:1, 2.5:1, 2.6:1, 2.7:1, 2.8:1, 2.9:1, 3.0:1, 3.1:1, 3.2:1, 3.3:1, 3.4:1, 3.5:1, 3.6:1, 3.7:1, 3.8:1, 3.9:1, 4.0:1, 4.1:1, 4.2:1, 4.3:1, 4.4:1, 4.5:1, 4.6:1, 4.7:1, 4.8:1, 4.9:1, 5.0:1, 5.1:1, 5.2:1, 5.3:1, 5.4:1, 5.5:1, 5.6:1, 5.7:1, 5.8:1, 5.9:1, 6.0:1, 6.1:1, 6.2:1, 6.3:1, 6.4:1, 6.5:1, 6.6:1, 6.7:1, 6.8:1, 6.9:1, 7.0:1, 7.1:1, 7.2:1, 7.3:1, 7.4:1, 7.5:1, 7.6:1, 7.7:1, 7.8:1, 7.9:1, 8.0:1, 8.1:1, 8.2:1, 8.3:1, 8.4:1, 8.5:1, 8.6:1, 8.7:1, 8.8:1, 8.9:1, 9.0:1, 9.1:1, 9.2:1, 9.3:1, 9.4:1, 9.5:1, 9.6:1, 9.7:1, 9.8:1, 9.9:1, 10.0:1, 11:1, 12:1, 13:1, 14:1, 15:1, 16:1, 17:1, 18:1, 19:1, 20:1, 25:1, 30:1, 35:1, 40:1, 45:1, 50:1, 55:1, 60:1, 65:1, 70:1, 75:1, 80:1, 85:1, 90:1, 95:1, or 100:1.

In certain embodiments, the composition, such as a neutraceutical or a dietary supplement, comprises C16:1n7-palmitoleate and its derivatives and further comprises C18:1n7-vaccenoate and its derivatives. The composition may comprise either more, less, or substantially the same amount of C16:1n7-palmitoleate and its derivatives relative to C18:1n7-vaccenoate and its derivatives. Typically, the composition comprises C16:1n7-palmitoleate and its derivatives relative to C18:1n7-vaccenoate and its derivatives in a ratio in excess of 1:1. In certain embodiments, the composition comprises a ratio of C16:1n7-palmitoleate and its derivatives relative to C18:1n7-vaccenoate and its derivatives (i.e., palmitoleate:C18:1n7-vaccenoate), wherein the ratio is in excess of 1.1:1, 1.2:1, 1.3:1, 1.4:1, 1.5:1, 1.6:1, 1.7:1, 1.8:1, 1.9:1, 2.0:1, 2.1:1, 2.2:1, 2.3:1, 2.4:1, 2.5:1, 2.6:1, 2.7:1, 2.8:1, 2.9:1, 3.0:1, 3.1:1, 3.2:1, 3.3:1, 3.4:1, 3.5:1, 3.6:1, 3.7:1, 3.8:1, 3.9:1, 4.0:1, 4.1:1, 4.2:1, 4.3:1, 4.4:1, 4.5:1, 4.6:1, 4.7:1, 4.8:1, 4.9:1, 5.0:1, 5.1:1, 5.2:1, 5.3:1, 5.4:1, 5.5:1, 5.6:1, 5.7:1, 5.8:1, 5.9:1, 6.0:1, 6.1:1, 6.2:1, 6.3:1, 6.4:1, 6.5:1, 6.6:1, 6.7:1, 6.8:1, 6.9:1, 7.0:1, 7.1:1, 7.2:1, 7.3:1, 7.4:1, 7.5:1, 7.6:1, 7.7:1, 7.8:1, 7.9:1, 8.0:1, 8.1:1, 8.2:1, 8.3:1, 8.4:1, 8.5:1, 8.6:1, 8.7:1, 8.8:1, 8.9:1, 9.0:1, 9.1:1, 9.2:1, 9.3:1, 9.4:1, 9.5:1, 9.6:1, 9.7:1, 9.8:1, 9.9:1, 10.0:1, 11:1, 12:1, 13:1, 14:1, 15:1, 16:1, 17:1, 18:1, 19:1, 20:1, 25:1, 30:1, 35:1, 40:1, 45:1, 50:1, 55:1, 60:1, 65:1, 70:1, 75:1, 80:1, 85:1, 90:1, 95:1, or 100:1.

In certain embodiments, the composition, such as a neutraceutical or a dietary supplement, comprises C16:1n7-palmitoleate and its derivatives and further comprises C18:1n9-oleate and its derivatives. The composition may comprise either more, less, or substantially the same amount of C16:1n7-palmitoleate and its derivatives relative to C18:1n9-oleate and its derivatives. In certain embodiments, the composition comprises substantially the same amount of C16:1n7-palmitoleate and its derivatives relative to C18:1n9-oleate and its derivatives. In further embodiments, the compositions comprise a ratio of C16:1n7-palmitoleate and its derivatives relative to C18:1n9-oleate and its derivatives, wherein the ratio is in excess of 1.0.

In some embodiments, the composition, such as a neutraceutical or a dietary supplement, comprises C16:1n7-palmitoleate and its derivatives and further comprises C18:1n9-oleate and its derivatives, wherein the ratio of the C16:1n7-palmitoleate derivative to the oleate derivative (i.e., palmitoleate:oleate) is from about 1.1:1 to about 50:1. In some embodiments, the ratio of the C16:1n7-palmitoleate derivative to the oleate derivative (i.e., palmitoleate:oleate) is at least about 1.25:1. In some embodiments, the ratio of the C16:1n7-palmitoleate derivative to the oleate derivative (i.e., palmitoleate:oleate) is from about 10:1 to about 20:1. In some embodiments, the ratio of the C16:1n7-palmitoleate derivative to the oleate derivative (i.e., palmitoleate:oleate) is from about 20:1 to about 50:1.

Alternatively, in certain embodiments, the composition comprises a ratio of C16:1n7-palmitoleate and its derivatives relative to C18:1n9-oleate and its derivatives (i.e., palmitoleate:oleate), wherein the ratio is in excess of 1.1:1, 1.2:1, 1.3:1, 1.4:1, 1.5:1, 1.6:1, 1.7:1, 1.8:1, 1.9:1, 2.0:1, 2.1:1, 2.2:1, 2.3:1, 2.4:1, 2.5:1, 2.6:1, 2.7:1, 2.8:1, 2.9:1, 3.0:1, 3.1:1, 3.2:1, 3.3:1, 3.4:1, 3.5:1, 3.6:1, 3.7:1, 3.8:1, 3.9:1, 4.0:1, 4.1:1, 4.2:1, 4.3:1, 4.4:1, 4.5:1, 4.6:1, 4.7:1, 4.8:1, 4.9:1, 5.0:1, 5.1:1, 5.2:1, 5.3:1, 5.4:1, 5.5:1, 5.6:1, 5.7:1, 5.8:1, 5.9:1, 6.0:1, 6.1:1, 6.2:1, 6.3:1, 6.4:1, 6.5:1, 6.6:1, 6.7:1, 6.8:1, 6.9:1, 7.0:1, 7.1:1, 7.2:1, 7.3:1, 7.4:1, 7.5:1, 7.6:1, 7.7:1, 7.8:1, 7.9:1, 8.0:1, 8.1:1, 8.2:1, 8.3:1, 8.4:1, 8.5:1, 8.6:1, 8.7:1, 8.8:1, 8.9:1, 9.0:1, 9.1:1, 9.2:1, 9.3:1, 9.4:1, 9.5:1, 9.6:1, 9.7:1, 9.8:1, 9.9:1, 10.0:1, 11:1, 12:1, 13:1, 14:1, 15:1, 16:1, 17:1, 18:1, 19:1, 20:1, 25:1, 30:1, 35:1, 40:1, 45:1, 50:1, 55:1, 60:1, 65:1, 70:1, 75:1, 80:1, 85:1, 90:1, 95:1, or 100:1.

In further embodiments, the composition comprises a ratio of C18:1n9-oleate and its derivatives relative to C16:1n7-palmitoleate and its derivatives, wherein the ratio is in excess of 1.0. For example, in certain embodiments, the composition comprises a ratio of C18:1n9-oleate and its derivatives relative to C16:1n7-palmitoleate and its derivatives (i.e., oleate:palmitoleate), wherein the ratio is in excess of 1.1:1, 1.2:1, 1.3:1, 1.4:1, 1.5:1, 1.6:1, 1.7:1, 1.8:1, 1.9:1, 2.0:1, 2.1:1, 2.2:1, 2.3:1, 2.4:1, 2.5:1, 2.6:1, 2.7:1, 2.8:1, 2.9:1, 3.0:1, 3.1:1, 3.2:1, 3.3:1, 3.4:1, 3.5:1, 3.6:1, 3.7:1, 3.8:1, 3.9:1, 4.0:1, 4.1:1, 4.2:1, 4.3:1, 4.4:1, 4.5:1, 4.6:1, 4.7:1, 4.8:1, 4.9:1, 5.0:1, 5.1:1, 5.2:1, 5.3:1, 5.4:1, 5.5:1, 5.6:1, 5.7:1, 5.8:1, 5.9:1, 6.0:1, 6.1:1, 6.2:1, 6.3:1, 6.4:1, 6.5:1, 6.6:1, 6.7:1, 6.8:1, 6.9:1, 7.0:1, 7.1:1, 7.2:1, 7.3:1, 7.4:1, 7.5:1, 7.6:1, 7.7:1, 7.8:1, 7.9:1, 8.0:1, 8.1:1, 8.2:1, 8.3:1, 8.4:1, 8.5:1, 8.6:1, 8.7:1, 8.8:1, 8.9:1, 9.0:1, 9.1:1, 9.2:1, 9.3:1, 9.4:1, 9.5:1, 9.6:1, 9.7:1, 9.8:1, 9.9:1, 10.0:1, 11:1, 12:1, 13:1, 14:1, 15:1, 16:1, 17:1, 18:1, 19:1, 20:1, 25:1, 30:1, 35:1, 40:1, 45:1, 50:1, 55:1, 60:1, 65:1, 70:1, 75:1, 80:1, 85:1, 90:1, 95:1, or 100:1.

In some embodiments, the composition, such as a neutraceutical or a dietary supplement, comprises C16:1n7-palmitoleate and its derivatives and further comprises a C16:4 hexadecatetradienoate derivative, wherein the ratio of the C16:1n7-palmitoleate derivative to the C16:4 hexadecatetradienoate derivative (i.e., palmitoleate:C16:4 hexadecatetradienoate) is from about 2:1 to about 50:1. In some embodiments, the ratio of the C16:1n7-palmitoleate derivative to the C16:4 hexadecatetradienoate (i.e., palmitoleate:C16:4 hexadecatetradienoate) is from about 2:1 to about 5:1. In some embodiments, the ratio of the C16:1n7-palmitoleate derivative to the C16:4 hexadecatetradienoate (i.e., palmitoleate:C16:4 hexadecatetradienoate) is from about 10:1 to about 30:1.

Alternatively, in certain embodiments, the composition comprises a ratio of C16:1n7-palmitoleate and its derivatives relative to C16:4 hexadecatetradienoate and its derivatives (i.e., palmitoleate:C16:4 hexadecatetradienoate), wherein the ratio is in excess of 1.1:1, 1.2:1, 1.3:1, 1.4:1, 1.5:1, 1.6:1, 1.7:1, 1.8:1, 1.9:1, 2.0:1, 2.1:1, 2.2:1, 2.3:1, 2.4:1, 2.5:1, 2.6:1, 2.7:1, 2.8:1, 2.9:1, 3.0:1, 3.1:1, 3.2:1, 3.3:1, 3.4:1, 3.5:1, 3.6:1, 3.7:1, 3.8:1, 3.9:1, 4.0:1, 4.1:1, 4.2:1, 4.3:1, 4.4:1, 4.5:1, 4.6:1, 4.7:1, 4.8:1, 4.9:1, 5.0:1, 5.1:1, 5.2:1, 5.3:1, 5.4:1, 5.5:1, 5.6:1, 5.7:1, 5.8:1, 5.9:1, 6.0:1, 6.1:1, 6.2:1, 6.3:1, 6.4:1, 6.5:1, 6.6:1, 6.7:1, 6.8:1, 6.9:1, 7.0:1, 7.1:1, 7.2:1, 7.3:1, 7.4:1, 7.5:1, 7.6:1, 7.7:1, 7.8:1, 7.9:1, 8.0:1, 8.1:1, 8.2:1, 8.3:1, 8.4:1, 8.5:1, 8.6:1, 8.7:1, 8.8:1, 8.9:1, 9.0:1, 9.1:1, 9.2:1, 9.3:1, 9.4:1, 9.5:1, 9.6:1, 9.7:1, 9.8:1, 9.9:1, 10.0:1, 11:1, 12:1, 13:1, 14:1, 15:1, 16:1, 17:1, 18:1, 19:1, 20:1, 25:1, 30:1, 35:1, 40:1, 45:1, 50:1, 55:1, 60:1, 65:1, 70:1, 75:1, 80:1, 85:1, 90:1, 95:1, or 100:1.

Compositions comprising C16:1n7-palmitoleate include dietary supplements, nutraceutical formulations, and pharmaceutical compositions.

In one embodiment, a composition is administered to a subject in an amount sufficient to provide a daily dose of C16:1n7-palmitoleate of about 1 mg to about 10,000 mg. In some embodiments, the daily dose of C16:1n7-palmitoleate is from about 50 mg to about 100 mg, or from about 100 mg to about 150 mg, or from about 150 mg to about 200 mg, or from about 200 mg to about 250 mg, or from about 300 mg to about 350 mg, or from about 400 mg to about 450 mg, or from about 450 mg to about 500 mg, or from about 500 mg to about 600 mg, or from about 600 mg to about 800 mg, or from about 800 mg to about 1,000 mg, or from about 1,000 mg to about 1,200 mg, or from about 1,200 mg to about 1,400 mg, or from about 1,400 mg to about 1,600 mg, or from about 1,600 mg to about 1,800 mg, or from about 1,800 mg to about 2,000 mg, or from about 2,000 mg to about 2,200 mg, or from about 2,200 mg to about 2,500 mg, or from about 2,500 mg to about 5,000 mg, or from about 5,000 mg to about 10,000 mg.

In one embodiment, a composition for use in methods described herein comprises C16:1n7-palmitoleate, or a pharmaceutically acceptable ester, derivative, conjugate or salt thereof, or mixtures of any of the foregoing. The term "pharmaceutically acceptable" in the present context means that the substance in question does not produce unacceptable toxicity to the subject or interaction with other components of the composition.

In another embodiment, C16:1n7-palmitoleate is present in a composition useful in accordance with methods described herein in an amount of about 50 mg to about 5000 mg In some embodiments, C16:1n7-palmitoleate is present in a composition useful in accordance with methods described herein in an amount of from about 50 mg to about 100 mg, or from about 100 mg to about 150 mg, or from about 150 mg to about 200 mg, or from about 200 mg to about 250 mg, or from about 300 mg to about 350 mg, or from about 400 mg to about 450 mg, or from about 450 mg to about 500 mg, or from about 500 mg to about 600 mg, or from about 600 mg to about 800 mg, or from about 800 mg to about 1,000 mg, or from about 1,000 mg to about 1,200 mg, or from about 1,200 mg to about 1,400 mg, or from about 1,400 mg to about 1,600 mg, or from about 1,600 mg to about 1,800 mg, or from about 1,800 mg to about 2,000 mg, or from about 2,000 mg to about 2,200 mg, or from about 2,200 mg to about 2,500 mg, or from about 2,500 mg to about 5,000 mg.

In another embodiment, a composition contains not more than about 10%, not more than about 9%, not more than about 8%, not more than about 7%, not more than about 6%, not more than about 5%, not more than about 4%, not more than about 3%, not more than about 2%, not more than about 1%, or not more than about 0.5%, by weight, palmitic acid, if any. In another embodiment, a composition contains substantially no palmitic acid. In still another embodiment, a composition contains no palmitic acid and/or derivative thereof.

In another embodiment, C16:1n7-palmitoleate comprises at least 70%, at least 80%, at least 90%, at least 95%, at least 96%, at least 97%, at least 98%, at least 99%, or 100%, by weight, of all fatty acids present in a composition.

Sources of C16:1n7-Palmitoleate and Derivatives Thereof

In another aspect, methods are provided for obtaining C16:1n7-palmitoleate and derivatives thereof. In certain embodiments, C16:1n7-palmitoleate and derivatives thereof are isolated, concentrated, and or purified from a source selected from the group consisting of one or more plants, animals, fish, or microorganisms. In other embodiments, the C16:1n7-palmitoleate moiety of the C16:1n7-palmitoleate derivative is obtained from a source selected from the group consisting of fish, *macadamia* nuts, sea buckthorn, tallow, algae, bacteria, yeast, or a combination thereof.

In certain embodiments, the C16:1n7-palmitoleate moiety of the C16:1n7-palmitoleate derivative is obtained from fish, fish oil, or purified fish oil concentrates. In some embodiments, the fish are selected from the group consisting of anchovies, menhaden, pollock, herring, cod, salmon, smelt, tuna, mackerel, krill, or a combination thereof. In one embodiment, the fish are anchovies. In certain embodiments, the purified fish oil concentrates have had substantially all Omega-3 fatty acid derivatives removed. In certain embodiments, the above-described compositions are derived from refined or fractionated fish oil, wherein the fish are selected from the group consisting of anchovies, menhaden, pollock, herring, cod, salmon, smelt, tuna, mackerel, krill, or a combination thereof. In certain embodiments, the above-described compositions are derived from anchovy oil.

Fish oils contain relatively small weight percentages of C16:1n7-palmitoleate, and do not appear to be a suitable source of concentrated C16:1n7-palmitoleate. However, in certain embodiments, methods were developed to concentrate C16:1n7-palmitoleate, to a surprising extent, from fish oil by: (a) obtaining fish oil comprising fatty acid derivatives; (b) removing substantially all of the polyunsaturated fatty acid derivatives from the fish oil; (c) reducing the concentration of saturated fatty acid derivatives from the fish oil; and (d) reducing the concentration of monounsaturated fatty acid derivatives other than C16:1n7-palmitoleate from the fish oil, to yield a composition derived from fish oil having a concentrated weight percentage of C16:1n7-palmitoleate. In certain embodiments, each of steps (b), (c), and (d), optionally and independently comprises the step of separating a fatty acid liquid derivatives from a fatty acid solid derivatives. In certain embodiments, each of steps (b), (c), and (d), optionally and independently comprises the step of treating fatty acid derivatives with hydroxide to convert some or all of the fatty acid derivatives into free fatty acids. In certain embodiments, each of steps (b), (c), and (d), optionally and independently comprises the step of treating fatty acid derivatives with acid (e.g., HCl) and alcohol (e.g., methanol, ethanol, or propanol) to convert some or all of the fatty acid derivatives into fatty esters (e.g., methyl ester, ethyl ester, or propyl ester). In certain embodiments, each of steps (b), (c), and (d), optionally and independently comprises the step of treating free fatty acid derivatives with a base (e.g., urea) to convert some or all of the free fatty acids into salts (e.g., urea salts) that can be precipitated and separated.

In certain embodiments, a dietary supplement comprising C16:1n7-palmitoleate, as described herein, is provided wherein the dietary supplement is prepared by a process comprising: (a) obtaining fish oil comprising fatty acid derivatives; (b) removing substantially all of the polyunsaturated fatty acid derivatives except C16:4 hexadecatetraenoate from the fish oil; (c) reducing the concentration of saturated fatty acid derivatives from the fish oil; and (d) reducing the concentration of monounsaturated fatty acid derivatives other than C16:1n7-palmitoleate from the fish oil, to obtain the dietary supplement as described herein comprising C16:1n7-palmitoleate. In certain embodiments, C16:4 hexadecatetradienoate is removed with substantially all of the polyunsaturated fatty acid derivatives. In certain embodiments, the wt % of the C16:1n7-palmitoleate derivative exceeds the wt % of any other single ingredient in the composition.

In certain embodiments, the dietary supplement is provided, wherein each of steps (b), (c), and (d), optionally and independently comprises a step selected from the group consisting of: (i) separating the fatty acid liquid derivatives from the fatty acid solid derivatives; (ii) treating the fatty acid derivatives with hydroxide to convert some or all of the fatty acid derivatives into free fatty acids; (iii) treating the fatty acid derivatives with acid (e.g., HCl) and alcohol (e.g., methanol, ethanol, or propanol) to convert some or all of the fatty acid derivatives into fatty esters (e.g., methyl esters, ethyl esters, or propyl esters); and (iv) treating the free fatty acids with a base (e.g., urea) to convert some or all of the free fatty acids into salts (e.g., urea salts), wherein the salts are precipitated.

In certain embodiments, the polyunsaturated fatty acid derivatives comprise C16:2 hexadecadienoic, C16:4 hexadecatetradienoic, C18:2 linoleic, α-linolenic acid (ALA), (8E, 10E,12Z)-octadeca-8,10,12-trienoic acid, C20:4 arachidonic, C20:5 eicosapentaenoic (EPA), C21:5 heneicosanoic, C22:2 docosadienoic, C22:3 docosatrienoic, C22:4 docosatetraenoic, C22:5 docosapentaenoic, and C22:6 docosahexaenoic (DHA). In certain embodiments, the polyunsaturated fatty acid derivatives comprise Omega-3 fatty acids. In certain embodiments, the saturated fatty acid derivatives comprise C14:0 mirystic acid, C16:0 palmitic acid, C18:0 stearic acid, C20:0 arachidic acid, and C22:0 behenic acid. In certain embodiments, monounsaturated fatty acid derivatives comprise cis-vaccenic acid (18:1 n7) and oleic acid (18:1 n9). In certain embodiments, the weight percentage of oleic acid (18:1 n9) is reduced relative to the weight percentage of C16:1n7-palmitoleate. In certain embodiments, the weight percentage of oleic acid (18:1 n9) is reduced relative to the weight percentage of C16:1n7-palmitoleate and cis-vaccenic acid (18:1 n7). In certain embodiments, the method of concentrating C16:1n7-palmitoleate, steps (a), (b), (c), and (d), are carried out in any order. In certain embodiments, the method of concentrating C16:1n7-palmitoleate is carried out in the following order: (a), (b), (c), and (d). In certain embodiments, the method of concentrating C16:1n7-palmitoleate is carried out in the following order: (a), (b), (d), and (c). In certain embodiments, the method of concentrating C16:1n7-palmitoleate comprises steps (a), (b), followed by multiple cycles of steps (c) and (d).

In another aspect is provided a dietary supplement comprising a C16:1n7-palmitoleate derivative, wherein the wt % of the C16:1n7-palmitoleate derivative exceeds the wt % of any other single ingredient in the dietary supplement, and wherein the dietary supplement prepared by a process comprising: (i) obtaining fish oil comprising fatty acid derivatives; (ii) removing substantially all C20:5n3 eicosapentaenoate (EPA) derivatives and C22:6n3 docosahexaenoate (DHA) derivatives from the fish oil; (iii) increasing the concentration of the C16:1n7-palmitoleate derivative to yield the dietary supplement. In certain embodiments, step (ii) is carried out before step (iii). In other embodiments, step (iii) is carried out before step (ii).

In certain embodiments, the increasing step comprises: (iv) treating the fish oil with alcohol and acid to convert substantially all of the remaining fatty acid derivatives into alkyl esters; (v) subjecting the alkyl esters to short path distillation and/or fractional distillation within a vacuum distillation tower to yield purified alkyl esters; (vi) treating the purified alkyl esters with urea; and (vii) recrystallizing the purified alkyl esters to yield the dietary supplement. In one embodiment, the alcohol is methanol and the alkyl esters are methyl esters. In another embodiment, the alcohol is ethanol and the alkyl esters are ethyl esters. In another embodiment, the acid is HCl.

As noted, provided herein are compositions comprising a C16:1n7-palmitoleate derivative, wherein the wt % of the C16:1n7-palmitoleate derivative exceeds the wt % of any other single ingredient in the composition. In other embodiments, compositions are provided comprising a C16:1n7-palmitoleate derivative, wherein the wt % of the C16:1n7-palmitoleate derivative exceeds the wt % of any other single ingredient in the composition and wherein the composition comprises additional fatty acids that extend the shelf-life of composition. In certain embodiments, 95 wt % of the C16:1n7-palmitoleate derivatives that are measured at an initial time point persist for at least six months, or at least one year, or at least eighteen months, or at least two years, or at least three years or at least five years. In certain embodiments, 90 wt % of the C16:1n7-palmitoleate derivatives that are measured at an initial time point persist for at least six months, or at least one year, or at least eighteen months, or at least two years, or at least three years or at least five years. In certain embodiments, 85 wt % of the C16:1n7-palmitoleate derivatives that are measured at an initial time point persist for at least six months, or at least one year, or at least eighteen months, or at least two years, or at least three years or at least five years.

In further embodiments, C16:1n7-palmitoleate and derivatives thereof are prepared from the enzymatic conversion of a precursor of C16:1n7-palmitoleate, such as C16:0-palmitate. In further embodiments, C16:1n7-palmitoleate and derivatives are chemically synthesized.

In certain embodiments, t methods are provided for obtaining C16:1n7-palmitoleate and derivatives thereof from plant oil such as those obtained from *macadamia* nuts (*Macadamia integrifolia*) or sea buckthorn (*Hippophae rhamnoides*). In certain embodiments, the C16:1n7-palmitoleate and derivatives thereof so obtained is fractionated to increase the concentration of the C16:1n7-palmitoleate and derivatives thereof relative to other plant oil constituents. In some embodiments, at least one step of the fractionation sequence is conducted at low-temperature. In some embodiments, all of the steps of the fractionation sequence are conducted at low-temperature.

In further embodiments, methods are provided for obtaining C16:1n7-palmitoleate and derivatives thereof from animal fat such as tallow. In certain embodiments, the C16:1n7-palmitoleate and derivatives thereof so obtained is fractionated to increase the concentration of the C16:1n7-palmitoleate and derivatives thereof relative to other tallow constituents. In some embodiments, at least one step of the fractionation sequence is conducted at low-temperature. In some embodiments, all of the steps of the fractionation sequence are conducted at low-temperature.

In still further embodiments, methods are provided for obtaining C16:1n7-palmitoleate and derivatives thereof from fish oil. In certain embodiments, the C16:1n7-palmitoleate and derivatives thereof so obtained is fractionated to increase the concentration of the C16:1n7-palmitoleate and derivatives thereof relative to other fish oil constituents. In certain embodiments, the fish oil undergoes a first processing step to remove or reduce the concentration of certain fatty acid constituents, such as the omega-3 fatty acids, e.g., α-linolenic acid, eicosapentaenoic acid, and docosahexaenoic acid, followed by a second processing step to increase the concentration of C16:1n7-palmitoleate and derivatives thereof. In some embodiments, at least one step of the fractionation sequence is conducted at low-temperature. In some embodiments, all of the steps of the fractionation sequence are conducted at low-temperature.

In still further embodiments, methods are provided for obtaining C16:1n7-palmitoleate and derivatives thereof from a microorganism. In certain embodiments, the microorganism is an algae. In certain embodiments, the microorganism is a yeast. In certain embodiments, the yeast is a strain of *Saccharomyces cerevisiae*. In certain embodiments, the microorganism is a bacterium. In certain embodiments, the bacterium is a strain of *Echerichia coli*. Methods for the production of fatty acids, such as C16:1n7-palmitoleate and derivatives thereof in *E. coli* are described in U.S. Patent Publication Nos. 2010/0274033, 2010/0257778, 2010/0257777, 2010/0251601, 2010/0249470, 2010/0242345, 2010/0235934, 2010/0221798, 2010/0199548, 2010/0170826, 2010/0105963, 2010/0071259, and 2008/0293060, the entire contents of each of which are incorporated herein by reference. In certain embodiments, the C16:1n7-palmitoleate and derivatives thereof so obtained is fractionated to increase the concentration of the C16:1n7-palmitoleate and derivatives thereof relative to other constituents of the microorganism. In some embodiments, at least one step of the fractionation sequence is conducted at low-temperature. In some embodiments, all of the steps of the fractionation sequence are conducted at low-temperature.

Pharmaceutical Compositions

In another aspect, pharmaceutical compositions are provided comprising C16:1n7-palmitoleate and derivatives thereof. The pharmaceutical compositions may also include a pharmaceutically acceptable excipient. The phrase "active ingredient" generally refers to a composition comprising C16:1n7-palmitoleate and derivatives thereof, as described herein.

As used herein, a "pharmaceutically acceptable form thereof" includes any pharmaceutically acceptable salts, solvates, hydrates, co-crystals, prodrugs, tautomers, isomers, and/or polymorphs of C16:1n7-palmitoleate and derivatives thereof, as defined below and herein.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of compounds of the compositions described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

The formulations of the pharmaceutical compositions described herein may be prepared by any method known or hereafter developed in the art of pharmacology. In general, such preparatory methods include the step of bringing the active ingredient into association with a carrier and/or one or more other accessory ingredients, and then, if necessary and/or desirable, shaping and/or packaging the product into a desired single- or multi-dose unit.

A pharmaceutical composition may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

The relative amounts of the active ingredient, the pharmaceutically acceptable carrier, and/or any additional ingredients in a pharmaceutical composition will vary, depending upon the identity, size, and/or condition of the subject treated and further depending upon the route by which the composition is to be administered. By way of example, the composition may comprise between 0.1% and 100% (w/w) active ingredient.

Exemplary pharmaceutically acceptable excipients include any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form. Remington's *The Science and Practice of Pharmacy*, 21$^{st}$ Edition, A. R. Gennaro, (Lippincott, Williams & Wilkins, Baltimore, Md., 2006) discloses various carriers used in formulating pharmaceutical compositions and known techniques for the preparation thereof. Except insofar as any conventional carrier medium is incompatible with a substance or its derivatives, such as by producing any undesirable biological effect or otherwise interacting in a deleterious manner with any other component(s) of the pharmaceutical composition, the use of any conventional carrier medium is contemplated.

In some embodiments, the pharmaceutically acceptable excipient is at least 95%, 96%, 97%, 98%, 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in the formulations. Excipients such as cocoa butter and suppository waxes, coloring agents, coating agents, sweetening, flavoring, and perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, chamomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include, but are not limited to, pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates are mixed with solubilizing agents such as Cremophor, alcohols, oils, modified oils, glycols, polysorbates, cyclodextrins, polymers, and combinations thereof.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polethylene glycols and the like.

The active ingredients can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient may be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, in a certain part of the intestinal tract, optionally, in a delayed manner. Examples of embedding compositions which can be used include polymeric substances and waxes.

Dosage forms for topical and/or transdermal administration of a compound may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as may be required. Additionally, contemplated herein is the use of transdermal patches, which often have the added advantage of providing controlled delivery of an active ingredient to the body. Such dosage forms may be prepared, for example, by dissolving and/or dispensing the active ingredient in the proper medium. Alternatively or additionally, the rate may be controlled by either providing a rate controlling membrane and/or by dispersing the active ingredient in a polymer matrix and/or gel.

Compositions comprising C16:1n7-palmitoleate or one or more derivatives thereof can be administered in a daily amount of from about 5 mg to about 10 mg, from about 10 mg to about 100 mg, from about 100 mg to about 500 mg, from about 0.5 g to about 1 g, from about 1 g to about 2 g, from about 2 g to about 4 g, from about 4 g to about 6 g, or from about 6 g to about 10 g.

In another embodiment, a composition as described herein is administered to a subject once or twice per day. In another embodiment, 1, 2, 3 or 4 capsules, each containing about 1 g of a composition as described herein, are administered to a subject daily. In another embodiment, 1 or 2 capsules, each containing about 1 g of a composition as described herein, are administered to the subject in the morning, for example between about 5 am and about 11 am, and 1 or 2 capsules, each containing about 1 g of a composition as described herein, are administered to the subject in the evening, for example between about 5 pm and about 11 pm.

Compositions can be formulated as one or more dosage units. The terms "dose unit" and "dosage unit" herein refer to a portion of a pharmaceutical composition that contains an amount of a therapeutic agent suitable for a single administration to provide a therapeutic effect. Such dosage units may be administered one to a plurality (i.e. 1 to about 10, 1 to 8, 1 to 6, 1 to 4 or 1 to 2) of times per day, or as many times as needed to elicit a therapeutic response.

In another embodiment, the use is provided of any composition described herein for treating moderate to severe hypertriglyceridemia in a subject in need thereof, comprising: providing a subject having a fasting baseline triglyceride level of about 500 mg/dl to about 1500 mg/dl and administering to the subject a pharmaceutical composition as described herein. In one embodiment, the composition comprising C16:1n7-palmitoleate or one or more derivatives thereof can be administered in a daily amount of from about 5 mg to about 10 mg, from about 10 mg to about 100 mg, from about 100 mg to about 500 mg, from about 0.5 g to about 1 g, from about 1 g to about 2 g, from about 2 g to about 4 g, from about 4 g to about 6 g, or from about 6 g to about 10 g.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

General considerations in the formulation and/or manufacture of pharmaceutical agents may be found, for example, in *Remington: The Science and Practice of Pharmacy* $21^{st}$ ed., Lippincott Williams & Wilkins, 2005.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation.

Still further encompassed are kits comprising one or more compounds (or pharmaceutically acceptable forms thereof), and/or a pharmaceutical composition described herein. Kits are typically provided in a suitable container (e.g., for example, a foil, plastic, or cardboard package). In certain embodiments, a kit may include one or more pharmaceutical excipients, pharmaceutical additives, therapeutically active agents, and the like, as described herein. In certain embodiments, a kit may include means for proper administration, such as, for example, graduated cups, syringes, needles, cleaning aids, and the like. In certain embodiments, a kit may include instructions for proper administration and/or preparation for proper administration.

While several embodiments have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the present teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, the aspects and embodiments may be practiced otherwise than as specifically described and claimed. The present aspects and embodiments are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present aspects and embodiments.

Exemplary embodiments of the disclosure will be described in more detail by the following examples. These embodiments are exemplary of the disclosure, which one skilled in art will recognize is not limited to the exemplary embodiments.

EXAMPLES

Example 1

The Fractionation of *Macadamia* Nut Oil and Other Oils

Using U.S. Pat. No. 4,601,856 as a guide, the following process of solvent fractionation (crystallization), urea adduct formation, and partial preferential saponification was used to increase the concentration of C16:1n7-palmitoleate derivatives from *macadamia* nut oil. Similar processes are described below using other oils, such as fish oil, that contain C16:1n7-palmitoleate.

General Procedure for the Fractionation of *Macadamia* Nut Oil

*Macadamia* nut oil was fractionated into Intermediates A through YY as described below. Generally, triglycerides in the *macadamia* nut oil were converted into methyl esters, saponified with potassium hydroxide (KOH), and acidified with hydrochloric acid (HCl) to produce free fatty acids comprising saturated and unsaturated fatty acids. The saturated fatty acids were primarily removed from the unsaturated fatty acids by the selective conversion of the saturated fatty acids into urea salts that, under specific temperatures and concentrations, that were preferentially precipitated from solution. The concentration of palmitoleate esters was increased relative to other unsaturated fatty esters (e.g., oleate esters) by subjecting reaction mixtures to conditions (e.g., concentrations and temperatures) that selectively favored saponification of the other unsaturated fatty esters, relative to the palmitoleate esters, with potassium hydroxide (KOH).

Tables I, II, and III (below) show the results of the fractionation of *macadamia* nut oil into Intermediates A through YY. Specifically, the normalized fatty acid composition data, calculated mass of fatty acid material, and the mass and yield of palmitoleic acid is shown for Intermediates A through YY.

*Macadamia* Nut Oil Intermediates A-YY

Intermediate A (Crude *Macadamia* Nut Free Fatty Acids): *Macadamia* nut oil (430.7 g) was treated with potassium hydroxide in methanol. A methanol solution of the crude methyl esters (441.7 g) were recovered and the crude glycerol (57.5 g) in methanol was drained. The crude methyl esters were treated with KOH in water and heated. The resulting potassium soaps were treated with aqueous HCl and aqueous NaCl. The resulting *macadamia* nut free fatty acids (403.3 g) were recovered and dried over a steam table until they were clear with no visible water droplets or turbidity. Intermediate A, the *macadamia* nut free fatty acids (400.0 g, dried), contained C16:1n7 (79.5 g). Intermediate A was treated with urea (84.4 g, half charge of urea) in methanol (504 g) and heated until the mixture became clear, cooled, and filtered at room temperature. The resulting mixture was separated into a solid urea fraction (Intermediate B) and a liquid fraction (Intermediate C).

Intermediate B: The solid urea fraction (80.7 g wet) derived from Intermediate A, above, was air dried, yielding Intermediate B (72.0 g).

Intermediate BB: Intermediate B was treated with aqueous HCl, rinsed, and decanted, yielding Intermediate BB, containing C16:1n7 (2.9 g).

Intermediate C: The liquid fraction (874.1 g) derived from Intermediate A, above, contained C16:1n7 (80.5 g). To intermediate C was added urea (84.4 g, a half charge of urea) and methanol (189.9 g). The mixture was heated until clear, cooled, and filtered at 8° C. The resulting mixture was separated into a solid urea fraction (Intermediate D) and a liquid fraction (Intermediate E).

Intermediate D: The solid urea fraction (114.7 g wet) was air dried to yield Intermediate D (109.7 g).

Intermediate DD: Intermediate D was treated with aqueous HCl, rinsed, and decanted, yielding Intermediate DD, containing C16:1n7 (3.0 g).

Intermediate E: The liquid fraction (978.0 g) derived from Intermediate C, above, contained C16:1n7 (78.2 g). Intermediate E was treated with potassium hydroxide (18.5 g, est. 40% of oleic) in water (166.5 g), heated until clear, cooled, and filtered at −6° C. Due to poor fractionation, the resulting liquid and solid intermediates F and G were recombined, diluted with methanol (239.3 g), heated until clear, cooled, re-crystallized, and filtered at 0° C. The resulting mixture was separated into a liquid fraction (Intermediate H) and a "solid" potassium soap fraction (Intermediate J).

Intermediate J: The "solid" potassium soap fraction weighed 106.9 g wet and 89.3 g after being air dried.

Intermediate JJ: Intermediate J was treated with aqueous HCl, rinsed, and decanted, yielding Intermediate JJ (82.1 g wet), containing C16:1n7 (13.6 g).

Intermediate H: The liquid fraction (1369.7 g) derived from Intermediate E, above, contained C16:1n7 (56.7 g). Intermediate H was treated with potassium hydroxide (14.0 g, est. 70% of oleic) in methanol (136 g). The mixture was heated until it became clear, cooled and filtered at −1° C. The resulting mixture was separated into a "solid" potassium soap fraction (Intermediate K) and a liquid fraction (Intermediate L).

Intermediate K: The "solid" potassium soap fraction weighed 328.8 g wet.

Intermediate KK. Intermediate K was treated with aqueous HCl, rinsed, and decanted, yielding Intermediate KK (165.7 g wet), containing C16:1n7 (27.0 g).

Intermediate L: The liquid fraction (1110.3 g) derived from Intermediate H, above, contained C16:1n7 (30.4 g). Intermediate L was diluted in methanol (98.1 g) and heated until the mixture became clear, cooled, and filtered at −15° C. to recover more of soap fraction. The resulting mixture was separated into a "solid" potassium soap fraction (Intermediate M) and a liquid fraction (Intermediate N).

Intermediate M: The "solid" potassium soap fraction weighed 124.2 g wet and 54.0 g when air dried.

Intermediate MM: Intermediate M was treated with aqueous HCl, rinsed, and decanted, yielding Intermediate MM (38.1 g wet), containing C16:1n7 (9.6 g).

Intermediate N: The liquid fraction (1037.2 g) derived from Intermediate L, above, contained C16:1n7 (20.2 g).

Intermediate PP: Intermediate N was treated with aqueous HCl, rinsed with 12 liters water to yield Intermediate MM (44.1 g wet), containing C16:1n7 (19.7 g).

Intermediate Y: *Macadamia* nut oil (MNO; 2.8 g) was diluted with acetone (3.5 g) to yield Intermediate Y.

Intermediate YY: Intermediate Y was mixed, cool in the freezer, and decanted at −15° C. to yield Intermediate YY.

TABLE 1

Fractionated Macadamia Nut Oil Intermediates A-E

| Fatty acid | A | BB | C | DD | E |
|---|---|---|---|---|---|
| Lauric acid C12 | 0.08 | ND | 0.09 | ND | ND |
| Myristic acid C14 | 0.81 | 0.78 | 0.82 | 1.04 | 0.78 |
| Palmitic acid C16 | 8.12 | 13.90 | 7.91 | 23.47 | 6.28 |
| Palmitoleic acid C16:1n7 | 20.63 | 11.88 | 20.93 | 8.45 | 22.22 |
| Margaric acid C17 | ND | 0.06 | ND | 0.09 | ND |
| Stearic acid C18 | 2.54 | 8.52 | 2.25 | 13.15 | 1.11 |
| Elaidic acid C18:1n9 (trans) | ND | 0.08 | 0.11 | 0.14 | ND |
| Oleic acid C18:1n9 | 54.87 | 35.04 | 55.68 | 31.74 | 58.33 |
| Vaccenic acid C18:1n7 | 3.38 | 2.04 | 3.43 | 1.72 | 3.58 |
| Linoleic acid C18:2n6 | 2.40 | 1.28 | 2.48 | 0.73 | 2.67 |
| Arachidic acid C20 | 2.34 | 14.61 | 1.64 | 14.40 | 0.31 |
| Alpha linolenic acid C18:3n3 | 0.17 | 0.11 | 0.18 | ND | 0.19 |
| Gondolic acid C20:1 | 2.92 | 2.03 | 3.00 | 2.26 | 3.03 |
| Conjugated linoleic acid (CLA) | 0.73 | 0.57 | 0.82 | 0.52 | 1.28 |
| Homo-gamma linolenic Acid C20:3n6 | 0.39 | 4.00 | 0.18 | 1.54 | ND |
| Erucic acid C22:1n9 | 0.32 | 0.27 | 0.34 | 0.42 | 0.31 |
| Eicosatrienoic acid C20:3n3 | ND | ND | ND | ND | ND |
| Lignoceric acid C24 | 0.34 | 4.83 | 0.05 | 0.36 | ND |
| Docosahexaenoic acid C22:6n3 | ND | ND | ND | ND | ND |
| Fatty acid mass (g) | 385.2 | 24.0* | 384.6 | 35.6* | 352.1 |
| C16:1n7 mass (g) | 79.5 | 2.9 | 80.5** | 3.0 | 78.2 |
| Yield, C16:1n7 (%) based on starting fatty acids | 100 | 3.6 | 101** | 3.8 | 98.4 |

*estimated using a 3:1 ratio of urea:fatty acid
**the calculated starting weight may be slightly low due to fatty acid content variability
ND—not determined

TABLE II

Fractionated Macadamia Nut Oil Intermediates H-MM

| Fatty acid | H | JJ | KK | L | MM |
|---|---|---|---|---|---|
| Lauric acid C12 | ND | 0.06 | ND | ND | ND |
| Myristic acid C14 | 0.71 | 1.10 | 0.45 | 1.10 | 0.67 |
| Palmitic acid C16 | 3.29 | 15.69 | 3.58 | 2.74 | 3.70 |
| Palmitoleic acid C16:1n7 | 24.35 | 17.50 | 17.19 | 37.58 | 26.06 |
| Margaric acid C17 | ND | 0.05 | ND | ND | ND |
| Stearic acid C18 | 0.47 | 3.33 | 0.06 | ND | 0.17 |
| Elaidic acid C18:1n9 (trans) | ND | 0.13 | ND | ND | ND |
| Oleic acid C18:1n9 | 61.18 | 51.64 | 68.99 | 46.23 | 58.98 |
| Vaccenic acid C18:1n7 | 3.76 | 3.24 | 3.24 | 4.66 | 3.85 |
| Linoleic acid C18:2n6 | 2.88 | 2.11 | 1.79 | 4.80 | 2.06 |
| Arachidic acid C20 | ND | 1.01 | 0.24 | ND | ND |
| Alpha linolenic acid C18:3n3 | ND | 0.14 | 0.12 | ND | 0.13 |
| Gondolic acid C20:1 | 3.12 | 2.92 | 3.22 | 2.88 | 3.27 |
| Conjugated linoleic acid (CLA) | ND | 0.71 | 0.78 | ND | 0.72 |
| Homo-gamma linolenic Acid C20:3n6 | ND | 0.04 | ND | ND | ND |
| Erucic acid C22:1n9 | ND | 0.34 | 0.34 | ND | 0.33 |
| Eicosatrienoic acid C20:3n3 | ND | ND | ND | ND | ND |
| Lignoceric acid C24 | ND | ND | ND | ND | ND |
| Docosahexaenoic acid C22:6n3 | ND | ND | ND | ND | ND |
| Fatty acid mass (g) | 232.8 | 77.4 | 157.1 | 80.9 | 36.7 |
| C16:1n7 mass (g) | 56.7 | 13.6 | 27.0 | 30.4 | 9.6 |
| Yield, C16:1n7 (%) based on starting fatty acids | 71.3 | 17.0 | 34.0 | 38.3 | 12.0 |

ND—not determined

TABLE III

Fractionated Macadamia Nut Oil Intermediates N-YY

| Fatty acid | N | PP | YY | MNO |
|---|---|---|---|---|
| Lauric acid C12 | ND | 0.32 | ND | ND |

TABLE III-continued

Fractionated Macadamia Nut Oil Intermediates N-YY

| Fatty acid | Intermediate | | | |
|---|---|---|---|---|
| | N | PP | YY | MNO |
| Myristic acid C14 | ND | 1.50 | 0.89 | 0.83 |
| Palmitic acid C16 | 1.99 | 1.83 | 7.23 | 8.32 |
| Palmitoleic acid C16:1n7 | 48.39 | 46.99 | 24.55 | 21.53 |
| Margaric acid C17 | ND | ND | ND | — |
| Stearic acid C18 | ND | 0.07 | 1.88 | 2.54 |
| Elaidic acid C18:1n9 (trans) | ND | 0.08 | ND | — |
| Oleic acid C18:1n9 | 34.24 | 32.95 | 55.36 | 53.83 |
| Vaccenic acid C18:1n7 | 5.46 | 5.34 | 3.57 | 4.55 |
| Linoleic acid C18:2n6 | 7.20 | 7.10 | 2.95 | 2.30 |
| Arachidic acid C20 | ND | ND | 0.98 | 2.35 |
| Alpha linolenic acid C18:3n3 | ND | 0.57 | ND | ND |
| Gondolic acid C20:1 | 2.73 | 2.52 | 2.68 | 2.70 |
| Conjugated linoleic acid (CLA) | ND | 0.48 | ND | ND |
| Homo-gamma linolenic Acid C20:3n6 | ND | ND | 0.27 | 0.40 |
| Erucic acid C22:1n9 | ND | 0.22 | ND | 0.29 |
| Eicosatrienoic acid C20:3n3 | ND | ND | ND | ND |
| Lignoceric acid C24 | ND | ND | ND | 0.30 |
| Docosahexaenoic acid C22:6n3 | ND | ND | ND | ND |
| Fatty acid mass (g) | 41.8 | 41.8 | ND | ND |
| C16:1n7 mass (g) | 20.2 | 19.7 | ND | ND |
| Yield, C16:1n7 (%) based on starting fatty acids | 25.5 | 24.7 | ND | ND |

MNO—macadamia nut oil
ND—not determined

Example 2

The Purification of 16:1n7-Palmitoleate from Fish Oils

Batches of anchovy or menhaden oil were each refined into oils having an increased weight percentages of ethyl 16:1n7-palmitoleate according to the general procedure described below.

The batches of crude oil (anchovy or menhaden) first had substantially all C20:5n3 eicosapentaenoic acid and C22:6n3 docosahexaenoic acid removed according to methods generally known to one of ordinary skill.

The resulting oil was deacidified (e.g., by treatment with base or an aqueous basic wash) and, optionally, bleached. The deacidified product was treated with ethanol and acid (e.g., HCl) to convert substantially all of the fatty acid derivatives into ethyl esters. The ethyl esters were subjected to molecular distillation (i.e., short path distillation), fractional distillation (i.e., within a vacuum distillation tower), recrystallization (e.g., from urea solutions of methanol or ethanol), and a final purification step that yielded oils having an increased weight percentages of ethyl 16:1n7-palmitoleate. Analyses of representative batches of fish oil purified according to the above-described general procedure ("Purified Oils") are shown below in Tables IV and V.

TABLE IV

Ethyl Ester wt % From Fractionated Fish Oils

| | Purified Oils | | | |
|---|---|---|---|---|
| Fatty Acid | Anchovy I* | Anchovy II | Anchovy III | Menhaden I |
| C14:0 Myristic | 7.7 | 1.29 | 1.70 | 3.09 |
| C14:1 Myristoleic | 0.6 | 0.25 | 0.33 | 0.90 |
| C15:0 Pentadecanoic | 0.3 | 0.43 | 0.11 | 0.46 |
| C15:1 Pentadecenoic | 0.1 | 0.44 | ND | ND |
| C16:0 Palmitic | 3.2 | 5.29 | 0.60 | 1.37 |
| C16:1 Palmitoleic | 39.3 | 47.95 | 51.32 | 59.95 |
| C16:2 Hexadecadienoic | 1.0 | 2.30 | ND | ND |
| C16:4 Hexadecatetradienoic | 1.5 | 15.48 | 18.15 | 4.40 |
| C17:0 Margaric | 3.3 | 6.55 | 0.27 | ND |
| C17:1 Margaroleic | 3.6 | 8.80 | ND | ND |
| C18:0 Stearic | 0.3 | 0.00 | ND | ND |
| C18:1 Oleic | 24.0 | 4.74 | 1.13 | 1.67 |
| C18:1 Vaccenic | ND | ND | 0.30 | 0.79 |
| C18:2 Linoleic | 2.6 | 0.61 | ND | 0.64 |
| C18:3 Linolenic | 1.8 | 0.32 | 0.08 | 0.09 |
| C18:4 Octadecatetraenoic | 2.0 | 1.29 | 0.54 | 1.47 |
| C19:0 Nonadecanoic | 0.5 | 0.16 | ND | ND |
| C19:1 Nonadecenoic | 0.6 | 0.20 | ND | ND |
| C20:0 Arachidic | ND | 0.14 | ND | ND |
| C20:4 Arachidonic | 0 | 0.00 | ND | ND |
| C20:5 Eicosapentaenoic | 0 | 0.91 | 0.06 | 0.09 |
| Other Fatty Acids | 2.3 | 2.8 | — | — |
| Unidentified | — | — | 25.1 | 24.53 |

*The results shown are the average of six batches

In Table V below, average fatty ester content of the fractionated oil obtained from Example 2 is compared with the fatty acid content of several natural oils.

TABLE V

Fatty Acid Content (approximate wt %) From Natural Oils

| Source | C14:0 Myristic | C14:1n5 Myristoleic | C16:0 Palmitic | C16:1n7 Palmitoleic | C18:0 Stearic | C18:1n9 Oleic | C18:2n6 Linoleic |
|---|---|---|---|---|---|---|---|
| Natural Oils | | | | | | | |
| Anchovy | 7 | 0.1 | 17 | 9 | 3 | 10 | 1 |
| Menhaden | 8 | 0 | 15 | 11 | 4 | 15 | 2 |
| Herring | 7 | 0 | 12 | 10 | 1 | 12 | 1 |
| Cod Liver | 4 | 0 | 11 | 8 | 3 | 21 | 1 |
| Macadamia Nut | 0.5 | 0 | 9 | 17 | 3 | 65 | 2 |
| Sea Buckthorn | 0 | 0 | 22 | 20 | 2 | 24 | 26 |
| Soy bean | 0 | 0 | 11 | <0.1 | 4 | 23 | 5 |

TABLE V-continued

| | Fatty Acid Content (approximate wt %) From Natural Oils | | | | | | |
|---|---|---|---|---|---|---|---|
| Source | C14:0 Myristic | C14:1n5 Myristoleic | C16:0 Palmitic | C16:1n7 Palmitoleic | C18:0 Stearic | C18:1n9 Oleic | C18:2n6 Linoleic |
| Palm | 1 | 0 | 44 | 0.3 | 4 | 37 | 9 |
| Canola | 0 | 0 | 4 | 0.2 | 2 | 62 | 19 |
| Olive | 0 | 0 | 11 | 1.3 | 2 | 71 | 10 |
| | | | Purified Oils | | | | |
| Anchovy I | 7.7 | 0.6 | 3.2 | 39.3 | 0.3 | 24.0 | 2.6 |
| Anchovy II | 1.3 | 0.3 | 5.3 | 48.0 | 0 | 4.7 | 0.6 |
| Anchovy III | 1.7 | 0.3 | 0.6 | 51.3 | ND | 1.1 | ND |
| Menhaden I | 3.1 | 0.9 | 1.4 | 60.0 | ND | 1.7 | 0.6 |

Example 3

Treatment of Apo E Knockout Mice With C16:1n7-Palmitoleate

Methods

Thirty-four male Apo E knockout mice were obtained from Jackson Laboratories (Bar Harbor, Me.). The mice were fed with normal mouse chow until 2 months of age and randomly allocated into two groups (n=17 each). One group of mice was then fed a control Western high-fat diet (F5722, fat 20%, cholesterol 2.1 gm/kg). The other group was fed a composition comprising C16:1n7-palmitoleate (CCO-Oil 20 wt %, cholesterol 2.1 gm/kg). CCO-Oil has approximately 20 wt % C16:1n7-palmitoleate. The consistency of the food was a paste; it appeared to be enticing to the mice and well tolerated. Water was freely available throughout the course of the study. Blood samples were obtained 8 and 12 weeks after initiation of the diet. At 12 weeks, all mice were sacrificed by intraperitoneal injection of ketamine/xylazine. This protocol was approved by the Institutional Animal Care and Use Committee at Cleveland Clinic. Data were presented as mean±SD. Statistical analysis was performed with t-test. $P<0.05$ indicates statistical significance. No significant difference in body weight was observed at the baseline, 4 weeks and 12 weeks follow-up between the control and treatment groups ($P>0.05$).

Quantification of Aorta Lesions

The surface area of aorta occupied by atherosclerotic lesions was quantified by en face oil red 0 staining, using an approach modified from Palinski et al. After mice were killed, a catheter was inserted into the left ventricle and the arterial tree was perfused with PBS (25 ml), followed by 4% buffered formaldehyde (20 ml, PH 7.4) at a pressure of 100 mm Hg. Under a microscope (Leica M500) the entire aorta attached to the heart was dissected and the adventitial fat was dissected. The ascending aorta was transected, and the heart was placed in histo-choice for assessment of aortic root atherosclerosis. The remainder of the aorta was stained with Sudan IV.

Figure 1B:
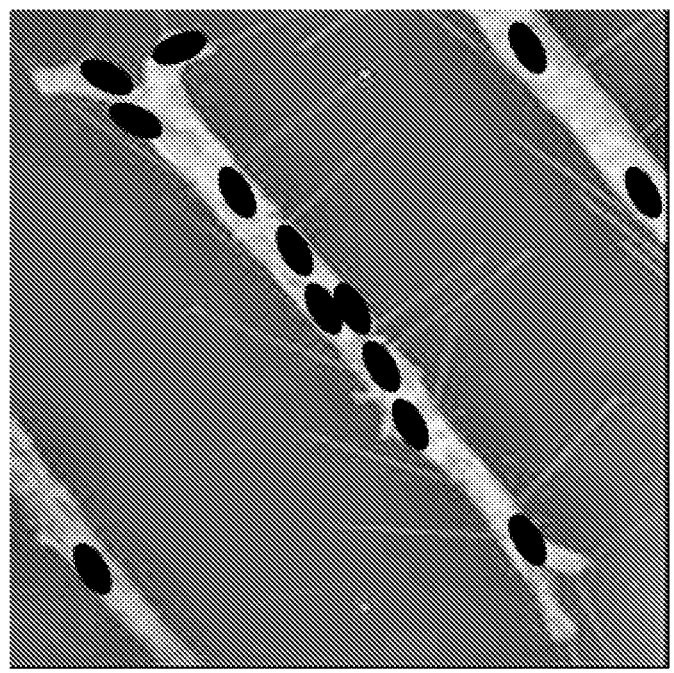
FIG. 1B illustrates the lack of significant cholesterol-derived plaques in the aorta of Apo-E knockout mice from the group that was fed a diet comprising C16:1n7-palmitoleate. The cholesterol-derived plaques were visualized by Sudan IV staining (The originally stained areas have been shaded with black ovals to improve visibility.) The extent of Sudan IV positive staining areas of the control treatment group that was fed a Western diet (in FIG. 1A) was significantly higher than the extent of positive staining in the group that was fed a diet comprising C16:1n7-palmitoleate (in FIG. 1B).

The aorta was opened longitudinally, pinned en face on a black silicone-covered dish, and photographed while immersed in PBS. See FIGS. 1A and 1B. The lesion area was quantified as the percent surface area occupied by Sudan IV red-staining using a computerized digital microscopic planimetry software package (Image-pro Plus, Version 4.0 for Windows, media Cybernetics, Silver Spring, Md.).

Quantification of Aortic Sinus Lesions

Figure 2B:
FIG. 2B illustrates the oil red O staining (shown as crosshatched) of the aortic root to detect atheromatous lesions in mice that received a diet comprising C16:1n7-palmitoleate. There is a dramatic decrease in the degree of atherosclerosis in the aortic root sinus in animals that received a diet comprising C16:1n7-palmitoleate.
Figure 2A:
FIG. 2A illustrates the oil red O staining (shown as crosshatched) of the aortic root to detect atheromatous lesions in mice that received a control Western diet.
Figure 3:
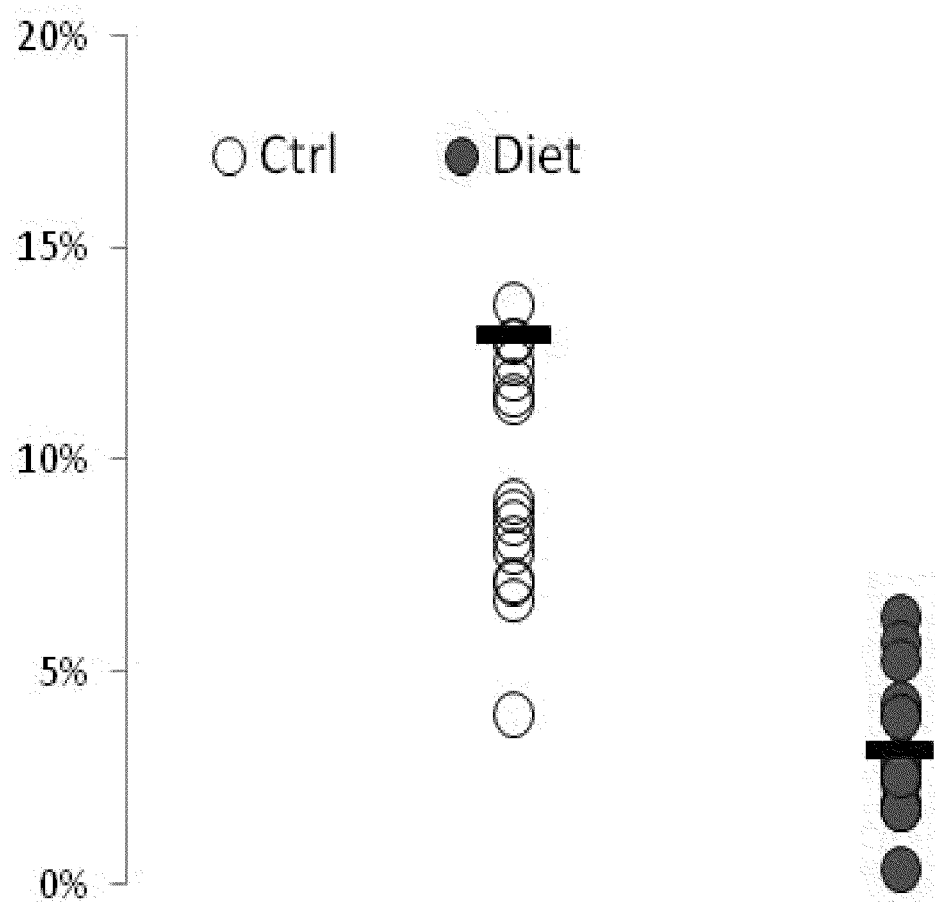
FIG. 3 illustrates data for lesion area in the descending thoracic aorta from mice fed a control Western diet ("Ctrl" open circles) and a diet comprising C16:1n7-palmitoleate ("Diet" i.e., a diet having 20 wt % CCO-Oil; shaded circles). Solid bars represent the mean lesion size. CCO-Oil has approximately 20 wt % C16:1n7-palmitoleate. Lesion areas were calculated as a percentage of the descending thoracic aorta.
Figure 4B:
FIG. 4 illustrates the relative aortic lesion size in Apo-E knockout mice following treatment with either (A) fish oil or (B) a composition comprising C16:1n7-palmitoleate. The red-stained aortic (shown as cross-hatched) lesion size is significantly reduced in Apo-E knockout mice following treatment with a composition comprising C16:1n7-palmitoleate.
Figure 4A:
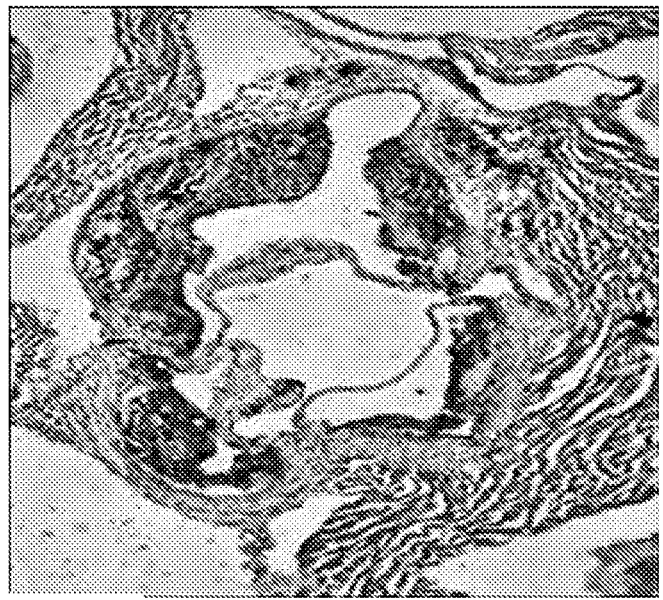

After fixation in histo-choice, the hearts were placed in optimum cutting temperature (OCT) compound, and frozen on dry ice. Cryostat sections (10 μm), starting at the apex and progressing through the aortic valve area into the ascending aorta, were cut at the level of the aortic sinus, collected on superfrost microscopic glass slides, and stored at −20° C. until analyzed. Sections were stained with oil red O and hematoxylin (Sigma) and counterstained with light green (Sigma). See FIGS. 2A and 2B. With the aortic sinus, lesions from 5 sections, each 80 μm apart were measured, using a computerized digital microscopic planimetry software package (Image-pro Plus, Version 4.0 for Windows, media Cybernetics, Silver Spring, Md.).

Assays for Serum Lipids

Serum samples, obtained from the tail vein of the mouse, were collected at the start of the study and at the 2-month time point. Serum samples were also obtained upon euthanasia at 3 months by cardiac puncture. All serum samples were individually evaluated for blood lipids. Enzymatic in vitro tests for the direct quantitative determination of triglycerides, cholesterol, and HDL-cholesterol on Roche automated clinical chemistry analyzers were used. All reagents were from Roche Diagnostics (Indianapolis, Ind.) and the instrument used was a Hitachi 911. The assays all used colorimetric methods with calibrated standards also from Roche, which were NIST (the National Institute of Standards) traceable. The results of the assays were further verified using the CDC (the Center for Disease Control) lipid standardization program.

Blood Lipid Levels

Table VI shows the resulting serum concentrations of blood lipids. There were not significant differences between the levels of total cholesterol and total triglycerides between the two groups at 8 weeks and at 12 weeks. However, HDL-cholesterol levels in the experimental treatment group was significantly increased compared to the baseline and the control group at 8 and 12 weeks follow-up ($P<0.01$).

TABLE VI

Levels of blood lipids at baseline, 8 weeks, and 12 weeks for animals that received Control Western diet and a Treatment diet (C16:1n7-palmitoleate).

| | Chol (mg/dL) | Trig (mg/dL) | HDL (mg/dL) |
|---|---|---|---|
| Baseline | | | |
| Control | 248.2 ± 63.1 | 108.1 ± 60.0 | 22.2 ± 6.8 |
| Treatment | 254.1 ± 58.2 | 107.1 ± 24.4 | 20.7 ± 6.9 |
| 8 weeks follow-up | | | |
| Control | 1021.3 ± 231.3 | 132.9 ± 51.3 | 25.3 ± 4.4 |
| Treatment | 960.4 ± 178.1 | 135.4 ± 39.3 | 40.3 ± 6.9* |

TABLE VI-continued

Levels of blood lipids at baseline, 8 weeks, and 12 weeks for animals that received Control Western diet and a Treatment diet (C16:1n7-palmitoleate).

|  | Chol (mg/dL) | Trig (mg/dL) | HDL (mg/dL) |
|---|---|---|---|
| 12 weeks follow-up |  |  |  |
| Control | 944.3 ± 238.3 | 112.7 ± 44.0 | 20.4 ± 6.5 |
| Treatment | 891.8 ± 181.5 | 100.1 ± 47.0 | 36.2 ± 9.8* |

Compared to the control *P < 0.01

Atherosclerotic Lesion Formation

Oil red O staining of aortic root displayed severe atherosclerosis of the aortic sinus in the control group (Table VII). The treatment group revealed significant reductions in atherosclerotic lesion by 47% relative to the control group (the control 0.33±0.09 vs the treatment 0.18±0.07 mm2, $P<0.001$). Atherosclerotic lesion area in the aorta of the experimental treatment group was also significantly inhibited (Table VIII; control 9.63±2.80% vs treatment 3.17±1.60%, $P<0.001$).

TABLE VII

Aortic sinus lesion size (mm²)

|  | Control | Treatment |
|---|---|---|
| C16:1n7-Palmitoleate | 0.33 ± 0.09 | 0.18 ± 0.07** |
| Rosuvastatin (20 mg/kg/day) | 0.36 ± 0.10 | 0.35 ± 0.10 |

TABLE VIII

Aortic lesion (%)

|  | Control | Treatment |
|---|---|---|
| C16:1n7-Palmitoleate | 9.63 ± 2.8 | 3.17 ± 1.6** |
| Rosuvastatin (20 mg/kg/day) | 21.9 ± 2.9 | 11.9 ± 1.9* |

Compared to the control group,
*P < 0.05,
**P < 0.00

Treatment with C16:1n7-palmitoleate showed a significant increase in the HDL-cholesterol at 8 and 12 weeks follow-up compared to the control group. Further, treatment with C16:1n7-palmitoleate appeared to significantly inhibit the atherosclerotic formation at the aortic root and dramatically decrease the atherosclerotic area of aorta in atherogenic apoE-deficient mice.

REFERENCES

Palinski W, et al., *Arterioscler. Thromb. Vasc Biol.* 1995; 15(10):1569-76.
Enomoto S, et al., *Biomed. Pharmacother.* 2009 January; 63(1):19-26.
Motoyama K, et al., *Nutrition;* 2009 April; 25(4):421-7.

Example 4

Effects of C16:1n7-Palmitoleate Upon the Plasma Concentrations of HDL and LDL in Human Subjects Six human volunteers had their plasma concentrations of HDL and LDL measured by each volunteer's medical practitioner. The six volunteers then consumed approximately two tablespoons per day of oil comprising approximately 20 wt % C16:1n7-palmitoleate for approximately one month. Plasma concentrations of HDL and LDL were subsequently remeasured by each volunteer's medical practitioner. Although uncontrolled, the study results, as shown below in Table IX, demonstrate that the administration of C16:1n7-palmitoleate yielded increases in the plasma concentration of HDL and decreases in the plasma concentration of LDL.

TABLE IX

| Subject | Age | Statin Use | Preventative Maintenance | HDL Base | Tx | % | LDL Base | Tx | % |
|---|---|---|---|---|---|---|---|---|---|
| Male | 72 | Yes | Yes | 44 | 51 | +16% | 82 | 61 | −23% |
| Male | 67 | No | No | 36 | 44 | +22% | 119 | 110 | −8% |
| Female | 70 | Yes | Yes | 38 | 44 | +16% | 104 | 92 | −12% |
| Male | 70 | Yes | Yes | 33 | 38 | +15% | ND | ND | ND |
| Male | 54 | No | No | 43 | 48.5 | +11.3% | 224 | 192 | −14% |
| Male |  |  |  | 30 | 37 | +23% | 129 | 100 | −22% |

ND—Not determined

Example 5

The Effects of Provinal™ on Fasting Human Subjects

Approximately thirty human subjects are enrolled in a study to assess the efficacy of Provinal™ (concentrated form of ethyl palmitoleate and other fatty esters derived from fish oil sources) on high-density lipoprotein cholesterol (HDL-C) concentrations. Other variables of the fasting lipoprotein lipid and glucose profiles are also measured. The human subjects include men and women between the ages of 21-75.

The subjects are evaluated based on baseline measurements compared to intervention with one daily dosage level of Provinal™ (e.g., 500-1,000 mg/day of Provinal™ 40, having approximately 200-400 mg ethyl palmitoleate, or 500-1,000 mg/day of Provinal™ 35, having approximately 175-350 mg ethyl palmitoleate, over a 90-day period). Generally, men will have baseline HDL-C levels at or below about 40 and women will have baseline HDL-C levels at or below about 50.

HDL-C concentrations, and changes thereto, are measured in all subjects. The following secondary variables are also be measured in blood plasma: HDL particle number, LDL concentration, LDL particle number, triglycerides, ApoB, ApoA1, tumor necrosis factor (TNF), hemoglobin A1c, and high sensitivity C-reactive protein (hsCRP). Data show that intervention with one daily dosage level of Provinal™ demonstrate a surprising increase in the concentration of HDL and decrease in the concentration in LDL.

Inclusion Criteria:

Generally, subjects are enrolled and remain in the study if they maintain consistent behavior throughout the duration of the study. Enrolled subjects who take additional medications are urged to maintain, if possible, a consistent medication regimen throughout the evaluation. Enrolled subjects adhere to fasting level requirements. Enrolled subjects who smoke agree not to alter their smoking habits during the evaluation.

Exclusion Criteria:

Generally, subjects are excluded who: experience medication regimen changes during the evaluation period that may alter HDL-C levels in plasma; do not adhere to fasting level requirements; become hospitalized for any reason; demonstrate symptoms of an inflammatory process that increase during the evaluation, including viral syndromes; have a known allergy to fish; are exposed to an investigational drug within 30 days of the evaluation; or have a history of alcohol or substance abuse. Females subjects are excluded who are pregnant or plan to become pregnant during the evaluation.

Example 6

The Chemical Stability of C16:1n7-Palmitoleate in Provinal™

Compositions comprising C16:1n7-palmitoleate are subjected to stability testing in which the molar concentration or wt % of C16:1n7-palmitoleate derivatives are measured at an initial time point and at one or more successive time points thereafter (e.g., once per week, once per month, once per six months, or once per year) to measure, as a function of time, the chemical stability of the C16:1n7-palmitoleate derivatives. The compositions comprising C16:1n7-palmitoleate are optionally subjected to elevated temperatures (e.g., 30° C., 40° C., 50° C., 60° C., 80° C.) during stability testing. The C16:1n7-palmitoleate derivatives in the compositions described herein have improved stability (i.e., shelf-life) relative to relatively pure (99%) C16:1n7-palmitoleate derivatives.

The foregoing written specification is considered to be sufficient to enable one skilled in the art to practice the present aspects and embodiments. The present aspects and embodiments are not to be limited in scope by examples provided, since the examples are intended as a single illustration of one aspect and other functionally equivalent embodiments are within the scope of the disclosure. Various modifications in addition to those shown and described herein will become apparent to those skilled in the art from the foregoing description and fall within the scope of the appended claims. The advantages and objects described herein are not necessarily encompassed by each embodiment. Those skilled in the art will recognize, or be able to ascertain using no more than routine experimentation, many equivalents to the specific embodiments described herein. Such equivalents are intended to be encompassed by the following claims.

All references disclosed herein are incorporated by reference in their entirety.

What is claimed is:

1. A dietary supplement comprising a C16:1n7-palmitoleate derivative and a palmitate derivative; wherein the supplement
   i) has a ratio of the C16:1n7-palmitoleate derivative to the palmitate derivative of 20:1 to 100:1; and
   (ii) comprises at least 20 wt % of the C16:1n7-palmitoleate derivative; and
   each palmitoleate and palmitate derivative is independently a free acid, pharmaceutically acceptable salt, ($C_1$-$C_4$)alkyl ester, monoglyceride, diglyceride, triglyceride, or a combination of any two or more thereof.

2. The dietary supplement of claim 1, comprising at least 35 wt % of the C16:1n7-palmitoleate derivative.

3. The dietary supplement of claim 1, comprising at least 50 wt % of the C16:1n7-palmitoleate derivative.

4. The dietary supplement of claim 1, comprising at least 90 wt % of the C16:1n7-palmitoleate derivative.

5. The dietary supplement of claim 1, wherein the ratio of the C16:1n7-palmitoleate derivative to the palmitate derivative is 20:1 to 50:1.

6. The dietary supplement of claim 1, wherein the ratio of the C16:1n7-palmitoleate derivative to the palmitate derivative is 50:1 to 100:1.

7. The dietary supplement of claim 1, wherein all of the derivatives are ($C_1$-$C_4$)alkyl esters.

8. The dietary supplement of claim 1, wherein all of the derivatives are ethyl esters.

9. The dietary supplement of claim 1, wherein all of the derivatives are methyl esters.

10. The dietary supplement of claim 1, wherein all of the derivatives are free acids or pharmaceutically acceptable salts thereof.

11. The dietary supplement of claim 1, wherein all of the derivatives are monoglycerides, diglycerides, triglycerides or a combination of any two or more thereof.

12. The dietary supplement of claim 1, wherein the C16:1n7-palmitoleate derivative is a cis-C16:1n7-palmitoleate derivative.

13. The dietary supplement of claim 1, wherein the supplement further comprises an oleate derivative, wherein the supplement has a ratio of the C16:1n7-palmitoleate derivative to the oleate derivative of 6:1 to 100:1, and each oleate derivative is independently a free acid, pharmaceutically acceptable salt, ($C_1$-$C_4$)alkyl ester, monoglyceride, diglyceride, triglyceride or a combination of any two or more thereof.

14. The dietary supplement of claim 13, wherein the ratio of the C16:1n7-palmitoleate derivative to the oleate derivative is 10:1 to 20:1.

15. The dietary supplement of claim 13, wherein the ratio of the C16:1n7-palmitoleate derivative to the oleate derivative is 20:1 to 50:1.

16. The dietary supplement of claim 13, wherein the ratio of the C16:1n7-palmitoleate derivative to the oleate derivative is 50:1 to 100:1.

17. The dietary supplement of claim 1, wherein the C16:1n7-palmitoleate derivative comprises a C16:1n7-palmitoleate moiety that is obtained from fish.

18. The dietary supplement of claim 17, wherein the fish are anchovies, menhaden, pollock, herring, cod, salmon, smelt, tuna, mackerel, krill or a combination of any two or more thereof.

19. The dietary supplement of claim 17, wherein the fish comprise anchovies.

20. The dietary supplement of claim 17, wherein the fish comprise menhaden.

* * * * *